US005629315A

United States Patent [19]
Bianco et al.

[11] Patent Number: 5,629,315
[45] Date of Patent: *May 13, 1997

[54] TREATMENT OF DISEASES USING ENANTIOMERICALLY PURE HYDROXYLATED XANTHINE COMPOUNDS

[75] Inventors: James A. Bianco, Seattle; Paul Woodson, Bothell; David Porubek, Edmonds; Jack Singer, Seattle, all of Wash.

[73] Assignee: Cell Therapeutics, Inc., Seattle, Wash.

[*] Notice: The portion of the term of this patent subsequent to Jun. 1, 2015, has been disclaimed.

[21] Appl. No.: 456,900

[22] Filed: Jun. 1, 1995

Related U.S. Application Data

[62] Division of Ser. No. 343,810, Nov. 22, 1994, abandoned, which is a division of Ser. No. 307,554, Sep. 16, 1994, abandoned, which is a continuation of Ser. No. 13,977, Feb. 4, 1993, abandoned, which is a continuation-in-part of Ser. No. 926,665, Aug. 7, 1992, abandoned, which is a continuation-in-part of Ser. No. 846,354, Mar. 4, 1992, abandoned.

[51] Int. Cl.$^6$ .................................................. A61K 31/52
[52] U.S. Cl. ........................................ 514/263; 514/866
[58] Field of Search ........................................ 514/263

[56] References Cited

U.S. PATENT DOCUMENTS

| | | | |
|---|---|---|---|
| 3,373,433 | 3/1968 | Mohler et al. | 343/850 |
| 3,422,107 | 1/1969 | Mohler et al. | 544/267 |
| 4,515,795 | 5/1985 | Hinze et al. | 514/263 |
| 4,525,309 | 6/1985 | Matteson et al. | 260/462 |
| 4,576,947 | 3/1986 | Hinze et al. | 514/263 |
| 4,636,507 | 1/1987 | Kreutzer et al. | 514/263 |
| 4,965,271 | 10/1990 | Mandell et al. | 514/263 |
| 5,096,906 | 3/1992 | Mandell et al. | 514/263 |
| 5,112,827 | 5/1992 | Saunders et al. | 514/263 |
| 5,118,500 | 6/1992 | Hänel et al. | 424/85.1 |
| 5,272,153 | 12/1993 | Mandell et al. | 514/263 |
| 5,310,666 | 5/1994 | Aretz et al. | 435/119 |
| 5,409,935 | 4/1995 | Schubert et al. | 514/265 |

FOREIGN PATENT DOCUMENTS

| | | |
|---|---|---|
| 435152 | 7/1991 | European Pat. Off. |
| 435153 | 7/1991 | European Pat. Off. |
| 3942872 | 6/1991 | Germany. |
| WO92/21344 | 12/1992 | WIPO. |

OTHER PUBLICATIONS

Bianco et al., *Blood*, vol. 78, No. 5, pp. 1205–1211, "Phase I–II Trial of Pentoxifylline for the Prevention of Transplant-Related Toxicities Following Bone Marrow Transplantation", 1991.

Davis et al., *Applied And Environmental Microbiology*, vol. 48, No. 2, pp. 327–331, "Microbial Models of Mammalian Metabolism: Microbial Reduction and Oxidation of Pentoxifylline", 1984.

Davis et al., *Xenobiotica*, vol. 15, No. 12, pp. 1001–1010, "Microbial Models of Mammalian Metabolism: Stereospecificity of Ketone Reduction with Pentoxifylline", 1985.

Matteson et al., *J. Am. Chem. Soc.*, vol. 108, pp. 810–819, "99% Chirally Selective Syntheses via Pinanediol Boronic Esters: Insect Pheromones, Diols, and an Amino Alcohol", 1986.

Soundarajan et al., *J. Org. Chem.*, vol. 55, pp. 2274–2275, "Hydroboration with Boron Halides and Trialkylsilanes", 1990.

*Primary Examiner*—Theodore J. Criares
*Attorney, Agent, or Firm*—Stephen Faciszewski

[57] ABSTRACT

There is disclosed compounds and pharmaceutical compositions that are a resolved R or S (preferably R) enantiomer of an $\omega$-1 alcohol of a straight chain alkyl ($C_{5-8}$) substituted at the 1-position of 3,7-disubstituted xanthine. The inventive compounds are effective in modulating cellular response to external or in situ primary stimuli, as well as to specific modes of administration of such compounds in effective amounts.

5 Claims, 22 Drawing Sheets

Figure 1. Mixed Leukocyte Reaction

Figure 2. B-Cell Proliferation

Figure 3. Thymocyte Proliferation

Figure 4. Smooth Muscle Cell Proliferation in Response to PDGF + IL-1

TREATMENT OF DISEASES USING ENANTIOMERICALLY PURE HYDROXYLATED XANTHINE COMPOUNDS

CROSS REFERENCE TO RELATED APPLICATIONS

This is a Division of U.S. application Ser. No. 08/343,810 filed 22 Nov. 1994, now abandoned, which is a Division of U.S. application Ser. No. 08/307,554, filed 16 Sep. 1994, now abandoned, which is a Continuation of U.S. Ser. No. 08/013,977 filed 04 Feb. 1993 now abandoned, which is a Continuation-In-Part of U.S. application Ser. No. 07/926,665 filed 07 Aug. 1992 now abandoned, which is a Continuation-in-Part of U.S. application Ser. No. 07/846,354 filed 04 Mar. 1992 now abandoned.

TECHNICAL FIELD OF THE INVENTION

The invention relates to a discovery that an isomer of a hydroxy-substituted xanthine compound is an effective agent to modulate cellular responses to stimuli mediated through a stereo-specific cellular second messenger pathway. More specifically, the inventive compounds are an R or S (preferably R) enantiomer of an ω-1 alcohol of a straight chain alkyl ($C_{5-8}$) substituted at the 1-position of 3,7-disubstituted xanthine. The inventive compounds are useful antagonism to control intracellular levels of specific sn-2 unsaturated phosphatidic acids and corresponding phosphatidic acids derived diacylglycerols which occur in response to cellular proliferative stimuli and mediated through a phosphotidic acid (PA) pathway.

BACKGROUND ART

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,307 and 3,737,433. Metabolites of PTX were summarized in Davis et at., *Applied Environment Microbiol.* 48:327, 1984. A metabolite of PTX is 1-(5-hydroxyhexyl)-3,7-dimethylxanthine, designated M1 and as a racemic mixture. M1 (racemic mixture) was also disclosed as increasing cerebral blood flow (as opposed to just increasing blood flow) in U.S. Pat. Nos. 4,515,795 and 4,576,947. In addition, U.S. Pat. Nos. 4,833,146 and 5,039,666 disclose use of shorter chain tertiary alcohol analogs of xanthine for enhancing cerebral blood flow. In subsequent metabolism studies, PTX was found to be metabolized to the S enantiomer.

Furthermore, U.S. Pat. No. 4,636,507 describes an ability of PTX and M1 (racemic mixture), to stimulate chemotaxis in polymorphonuclear leukocytes in response to a stimulator of cherootaxis. PTX and related tertiary alcohol substituted xanthines inhibit activity of certain cytokines to affect chemotaxis (U.S. Pat. No. 4,965,271 and U.S. Pat. No. 5,096,906). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

It is common practice to market a drug with a chiral center as a racemate. The M1 metabolite has only been disclosed exclusive of its chirality. In fact, M1 appears to be made (metabolically in humans) only as the S isomer. The approach of manufacturing and dosing drugs as racemic mixtures means that each dose of a drug is contaminated with an equal weight of an isomer, which usually has no therapeutic value and has the potential to cause unsuspected side effects. For example, the sedative thalidomide was marketed as a racemate. The desired sedative activity resided in the R-isomer, but the contaminating S-isomer is a teratogen, causing the birth defects in babies born to mothers using this drug. The R,R-enantiomer of the tuberculostatic ethambutol can cause blindness. The lethal side effects associated with the nonsteroidal anti inflammatory drug benoxaprofen (Oraflex) might have been avoided had the drug been sold as a pure enantiomer.

The issue of enantiomeric purity is not limited to the field of pharmaceuticals. For example, ASANA ($^i$Pr=isopropyl) is a synthetic pyrethroid insecticide which contains two asymetric centers. The potent insecticidal activity resides overwhelmingly in just one of four possible stereoisomers. Moreover, the three non-insecticidal stereoisomers exhibit cytotoxicity toward certain plant species. Therefore, ASANA can only be sold as a single stereoisomer because the mixed stereoisomers would not be suitable.

Therefore, there is a need in the art to discover effective therapeutic compounds that are safe and effective for human or animal administration and that can maintain cellular homeostasis in the face of a variety of inflammatory stimuli, and that are enantiomerically pure to have activity residing in a single isomer. The present invention was made in a process of looking for such compounds.

SUMMARY OF THE INVENTION

We have found that the compounds described herein can be used to maintain homeostasis of a large variety of target cells in response to a variety of inflammatory and proliferative stimuli. In addition, the inventive compounds and pharmaceutical compositions are suitable for normal routes of therapeutic administration (e.g., oral, topical and parenteral) and permit effective dosages to be provided.

The inventive compounds and pharmaceutical compositions are a resolved R or S (preferably R) enantiomer of an ω-1 alcohol of a straight chain alkyl ($C_{5-8}$) substituted at the 1-position of 3,7-disubstituted xanthine. The inventive compounds are effective in modulating cellular response to external or in situ primary stimuli, as well as to specific modes of administration of such compounds in effective amounts.

The inventive compounds comprise compounds and pharmaceutical compositions having a compound comprising a xanthine core of the formula:

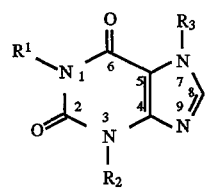

wherein $R_1$ is independently a resolved enantiomer ω-1 secondary alcohol-substituted alkyl ($C_{5-8}$) substantially free of the other enantiomer, and wherein each of $R_2$ and $R_3$ is independently alkyl ($C_{1-12}$) optionally containing one or two nonadjacent oxygen atoms in place of a carbon atom. Preferably $R_1$ is a $C_6$ alkyl with the hydroxyl group as the R enantiomer.

The present invention further provides a pharmaceutical composition comprising an inventive compound and a pharmaceutically acceptable excipient, wherein the pharmaceutical composition is formulated for oral, parenteral or topical administration to a patient.

The present invention further provides a method for treating an individual having a variety of diseases, wherein the disease is characterized by or can be treated by inhibiting an immune response or a cellular response to external or in situ primary stimuli, wherein the cellular response is mediated through a specific phospholipid-based second messenger acting adjacent to the inner leaflet of the cell membrane of a cell. The second messenger pathway is activated in response to various noxious or proliferative stimuli characteristic of a variety of disease states and the biochemistry of this second messenger pathway is described herein. More specifically, the invention is directed to methods to treat or prevent clinical symptoms of various disease states or reduce toxicity's of other treatments by inhibiting cellular signaling through the second messenger pathway described herein. The disease states or treatment-induced toxicity's are selected from the group consisting of proliferation of tumor cells in response to an activated oncogene; hematocytopenia caused by cytoreductive therapies or caused by an infection of a microbial agent; autoimmune diseases caused by a T cell response or a B cell response and antibody production; septic shock; resistance of mesenchymal cells to tumor necrosis factor (TNF); disregulation of cell activation or disregulated cell growth, such as proliferation of smooth muscle cells, endothelial cells, fibroblasts and other cell types in response to growth factors, such as PDGF-AA, BB, FGF, EGF, etc. (i.e., atherosclerosis, restenosis, stroke, and coronary artery disease); human immunodeficiency virus infection (AIDS and AIDS related complex); proliferation of kidney mesangial cells in response to IL-1, mip-1$\alpha$, PDGF or FGF resulting in various inflammatory renal diseases; inflammation; kidney glomerular or tubular toxicity in response to cyclosporin A or amphotericin B treatment; organ toxicity (e.g., gastrointestinal or pulmonary epithelial) in response to a cytoreductive therapy (e.g., cytotoxic drugs or radiation); enhancing antitumor effects of nonalkylating antitumor agents; allergies in response to inflammatory stimuli (e.g., TNF, IL-1 and the like) characterized by production of cell surface metalloproteases or by degranulation of mast cells and basophils in response to IgE, bone diseases caused by overproduction of osteoclast-activating factor (OAF) by osteoclasts, CNS diseases caused by reduced signal transduction of the neurotransmitters epinephrine and acetylcholine, arid combinations thereof.

When a cell is stimulated to express a particular cytokine or to proliferate in response to a proliferative or noxious stimuli, this process is mediated through a specific phospholipid-based second messenger signaling pathway. This second messenger pathway produces elevated levels of a subset of phosphatidic acid (PA) containing sn-2 non-arachidonate unsaturation that is rapidly converted to its corresponding diacylglycerol (DAG). The inventive compounds and pharmaceutical compositions specificly inhibit the stereo-specific enzymes involved in this second messenger pathway without affecting other second messenger pathways that are involved in normal house-keeping functions of a cell, such as the phosphatidyl inositol (PI) pathway. The result of inhibiting one or several enzymes involved in the second messenger pathway described herein is "modulation" of the response of a target cell to a stimulus, particularly a noxious stimulus. This biochemical event (i.e., inhibiting activity of a second messenger pathway enzyme that responds to a primary stimulus, such as a cytokine) effects cellular signaling and results in an effect upon many diverse disease states that are the result of abnormal, inflammatory or noxious cellular signaling mechanisms.

BRIEF DESCRIPTION OF THE DRAWINGS

FIG. 2 shows that CT1501R inhibited B-cell proliferation caused by the indicated proliferative signals.

FIG. 21 is the relative BCECF fluorescence (+/–SD) for each of the treatment groups.

FIG. 22 is the relative BCECF fluorescence (+/–SD) for each of the treatment groups.

DETAILED DESCRIPTION OF THE INVENTION

Figure 1:
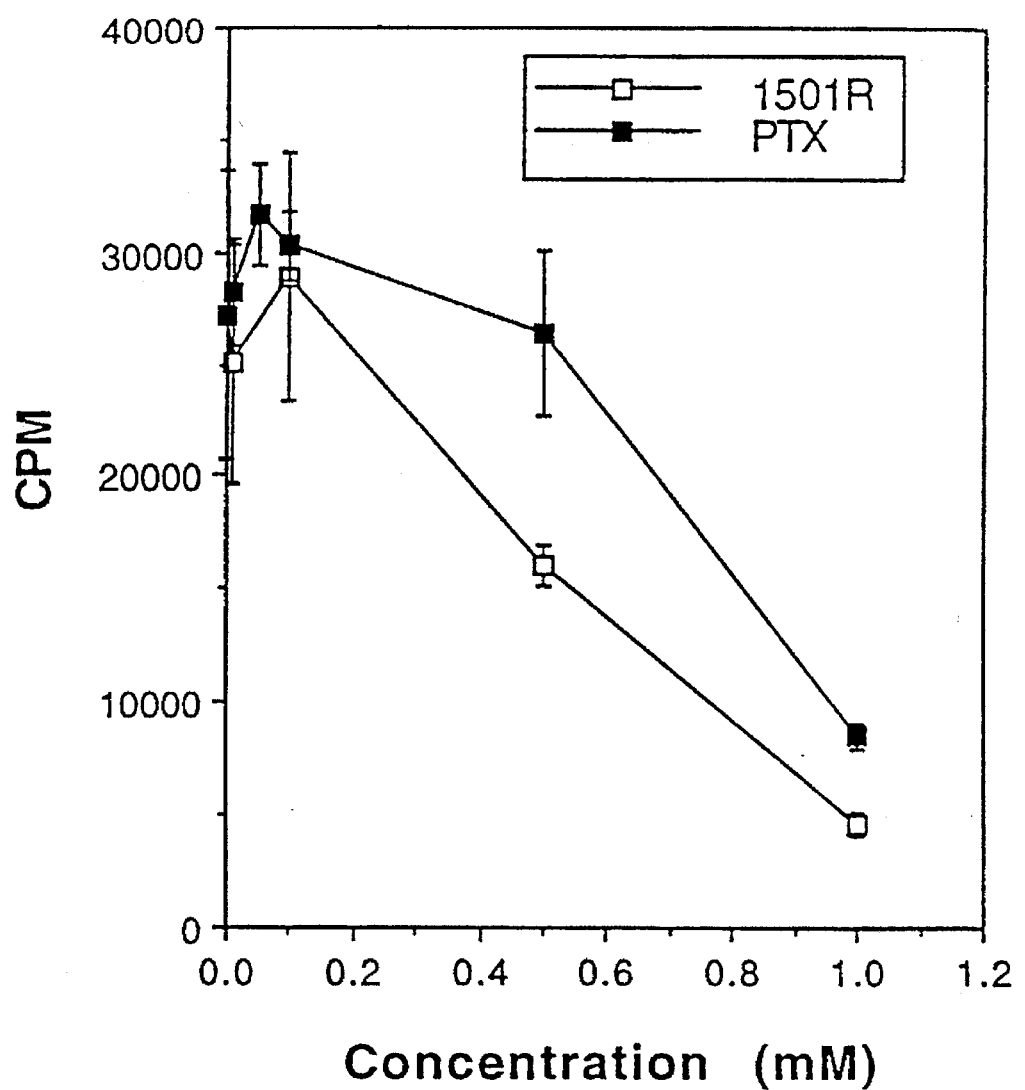
FIG. 1 shows a mixed lymphocyte reaction of CT1501R (R-(-)(5-hydroxyhexyl)theobromine) and PTX. The mixed lymphocyte reaction shows a proliferative response of PBMC (peripheral blood mononuclear cells) to allogeneic stimulation determined in a two-way mixed lymphocyte reaction. Both CT1501R and PTX showed dose-response activity in this immune modulating activity assay procedure.

The invention is directed to a defined genus of inventive compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=phosphatidyl choline "remodeled" PA, cyclic pathway=PAA, LPA, PA and DAG intermediates substituted with L-saturated, 2-linoleoyl or 1,2-dileolyl/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaneoyl-side chains.

Lysophosphatidic acid transferase CLPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT in PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl,2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH-and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmkate. In resting cells, PC's acyl side chains consist mostly of acyl palmirate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. However, it is important to know whether or not each phospholipid species passes through a PA form previous to hydrolysis to DAG. The lyso-PA that is converted to PA and thence to DAG may be shown. The complexities of this second messenger pathway can be sorted by suitable analyses by fatty acyl side chain chemistry (i.e., by thin layer chromatography or high pressure liquid chromatography) of intermediates in cells at various time points after stimulation of the second messenger pathway.

In certain mesengial cells, such as neutrophils and rat or human mesengial cells, several signaling pathways may be activated in tandem, simultaneously or both. For example, in neutrophils, F-Met-Leu-Phe stimulates formation of PA through the action of PLD, followed in time by formation of DAG through the action of PAPH. Several minutes later, DAG is generated from PI through the classical phosphoinositide pathway. In many cells, DAG is derived from both PA that is being remodeled through a cycle whereby PAA is sn-2 hydrolyzed by PLA-2, followed by sn-2 transacylation by LPAAT, and a PLD-pathway from PA that is generated from either PE or PC or both substrates by PLD.

Figure 12:
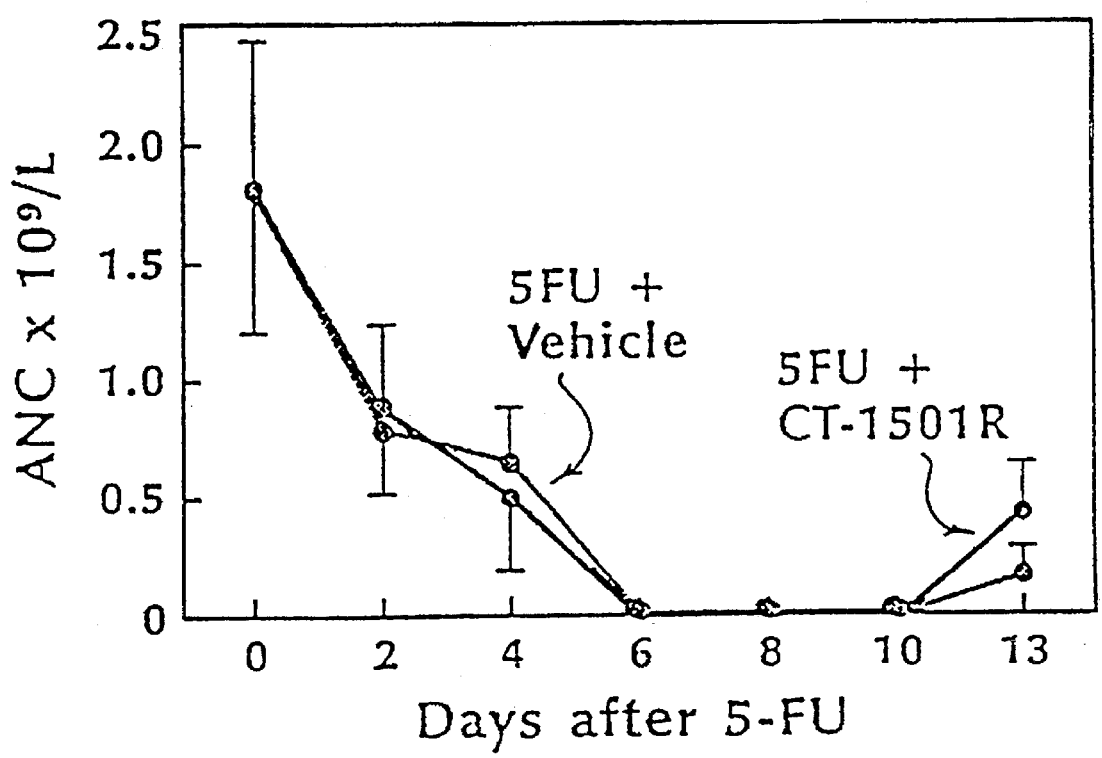
FIG. 12 shows the mean absolute neutrophil counts of mice treated with CT1501R or vehicle control twice daily starting on day 0. Groups of 4 mice were phlebotomized at each time point. The values on the graph represent the means±1 SD.

A method described here permits differentiation of the various subspecies of PA and DAG based upon acyl chain composition. This can differentiate those compounds that activate (and inhibit activation of) the present second messenger pathway from other pathways, such as the classical PI pathway. The present second messenger pathway involves substrates with unsaturated fatty acids in the sn-2 position other than arachidonate and those sub species of PAPH and LPAAT that are not involved in normal cellular housekeeping functions that are part of the classical PI pathway. The PAPH and LPAAT enzymes involved in the present second messenger pathway are exquisitely stereo specific for different acyl side chains and isomeric forms of substrates. Therefore, the inventive compounds are substantially enantiomerically pure, and preferably are the R enantiomer at the chiral carbon atom bonded to the hydroxyl group. For example, the R and S isomers of CT1501 have different LPAAT inhibiting activity as shown in FIG. 12. Further, the R enantiomer of CT1501 (e.g., CT1501R) is two to three time more potent than the racemic mixture (designated M1 herein), and many times more potent than the corresponding S enantiomer. Moreover, PTX is converted almost exclusively to the S enantiomer of MI when metabolized in humans or CT1501S.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway are not inhibited by the inventive compounds or PTX. In PTX-treated cells, DAG derived from remodeled and PLA-generated PA is diminished (e.g., 1,2-sn-dioleoyl DAG, 1-alkyl,2-linoleoyl DAG and 1-alkyl,2-docosahexaneolyl DAG). Therefore, the inventive compounds and PTX inhibit the formation of only a certain species of PA and DAG by selectively inhibiting a specific second messenger pathway that is only activated in cells by noxious stimuli, but is not used to signal normal cellular housekeeping functions.

Therapeutic Uses of the Inventive Compounds

The specific inhibition of activation of the specific second messenger pathway that is activated primarily by various noxious stimuli, provides the inventive compounds with an ability to be used to treat a wide variety of clinical indications. Moreover, the in vitro and in vivo data presented herein provides predictive data of a wide variety of clinical indications that share a common thread of activation of the specific second messenger pathway, whose activation by noxious stimuli mediated through, for exame, inflammatory cytokines, is specifically inhibited by the inventive compounds. In fact, it is this mechanism of action of the inventive compounds that explains why the inventive compounds can have a wide variety of different clinical indications. Activation of the present second messenger pathway is a major mediator of response to noxious stimuli and results in cellular signals that lead to, for example, inflammation, immune response, inhibition of blood cell regeneration and cancer cell growth. However, not all inhibitors inhibit all enzymes of this second messenger pathway. The inventive compounds are most effective mediators of inflammation and inhibition of blood cell regeneration. Signals mediated by the present second messenger pathway include, for example, those cellular responses of LPS directly, T cell activation by antigen, B cell activation by antigen, cellular responses to IL-1 mediated through the IL-1 Type 1 receptor (but not the IL-1 Type 2 receptor), the TNF Type 1 receptor, activated oncogenes (e.g., ras, abl, her2-neu and the like), low affinity GM-CSF (ganulocyte macrophage colony stimulating factor) receptor, and smooth muscle cell proliferation stimulated by PDGF, b-FGF and IL-1. Them are other signals that are not mediated through the present second messenger pathway, and these include proliferation of hematopoietic cells induced by G-CSF (granulocyte colony stimulating factor), interleukin-3 (IL-3), SCF (stem cell factor) and GM-CSF; neutrophil activation induced by interleukin-8 (IL-8) or leukotfiene B4; T cell proliferation in response to IL-2; and endothelial cell proliferation in response to acidic FGF (fibroblast growth factor).

In vitro, the inventive compounds: (1) block IL-1 signal transduction through the Type 1 receptor as shown, for example, by preventing IL-1 and IL-1 plus PDGF (platelet derived growth factor) induction of proliferation of smooth muscle and kidney mesengial cells; (2) suppresses up regulation of adhesion molecules as shown, for example, by blocking VCAM in endothelial cells of CD18 in neutrophils; (3) inhibiting TNF and IL-1 induced metalloproteases (an inflammation model); (4) block LPS-induced cellular activation (for prevention and treatment of septic shock); (5) suppress T cell and B cell activation by antigen of by cross-linking CD3 complex; (6) inhibit mast cell activation by IgE; and (7) suppress malignant phenotype in transformed cells and tumor cell lines.

The foregoing in vitro effects give rise to the following in vivo biologic effects, including, but not limited to, protection and treatment of endotoxic shock, inhibition of tumor cell growth, stimulation of hematopoiesis following cytoreductive therapy, synergistic immunosuppression in preventing GVHD (graft versus host disease), and stimulation of hair grow through reversal of an apoptotic process. There is in vivo data presented herein showing treatment and protection of endotoxic shock, stimulation of hematopoiesis following cytoreductive therapy and stimulation of hair growth in a nude mouse model. The inventive compounds, and particularly CT1501R, me most potent when used to stimulate hematopoiesis, prevent and treat septic shock and stimulate hair growth when applied topically. The inventive compounds are less potent and require higher molar concentrations for immunosuppression, acute inflammation, chronic inflammation and GVHD, although inhibitors of the present second messenger pathway can have such activities.

The inventive compounds also are useful as an adjuvant to inhibit toxic side effects of drugs whose side effects are mediated through the present second messenger pathway. These side effects include, for example, side effects of interleukin-2 (IL-2), renal side effects of cyclosporin A and FK506, and side effects of amphotericin B. It should be noted that the inventive compounds inhibit antigert-induced T cell activation, like cyclosporin of FK506, but, unlike cyclosporin or FK506, do not prevent generation of NK and LAK cells, do not suppress IL-2 release from T cells and do not suppress IL-8 release.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 kD type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, CT1501R reduced PUMP-1 activity induced by 100 U/ml of IL-1 to 15% of its control levels. PTX, by contrast in the same experiment, only inhibited PUMP-1 activity to 95% of its control levels which was not significant. Accordingly, the inventive compounds prevent induction of certain metalloproteases induced by IL-1 or TNF and are not involved with constitutively produced proteases (e.g., 72 kD type IV collagenase) involved in normal tissue remodeling.

The inventive compounds inhibit signal transduction mediated through the Type I IL-1 receptor, and are therefore considered as IL-1 antagonists. A recent review article entitled "The Role of Interleukin-1 in Disease" (Dinarello and Wolff N. Engl. J. Med. 328, 106, Jan. 14, 1993) described the role of IL-1 as "an important rapid and direct determinant of disease." "In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, "the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of LI-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of LI-1 also rapidly decreases blood pressure, and doses of 300 ng or more per kilogram of body weight may cause severe hypotension." "The therapeutic advantage of blocking the action of IL-1 resides in preventing its deleterious biologic effects without interfering with the production of molecules that have a role in homeostasis." The present inventive compounds address the need identified by Dr. Denarello by inhibiting cellular signaling only through the IL-1 Type I receptor and not through the IL-1 Type II receptor.

With regard to rheumatoid arthritis, Dr. Denarello states: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, inteleukin-1 triggers the expression of genes for collagenases as well as phospholipuses and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$) and leukotriene $B_4$ ($LTB_4$) and IL-8, an inflammatory cytokine with neutrophil-chemoattractant and neutrophil-stimulating properties. Tissue concentrations of PGE2 and LTB4 correlate with the severity of disease in patients with ulcerative colitis, and tissue concentrations of IL-1 and IL-8 are high in patients with inflammatory bowel disease. Therefore, an IL-1 antagonist, such as the inventive compounds, would be effective to treat inflammatory bowel disease.

With regard to acute and chronic myelogenous leukemia, there is increasing evidence that IL-1 acts as a growth factor for such tumor cells. Therefore, the inventive compounds should be effective to prevent the growth of worsening of disease for acute and chronic myelogenous leukemias.

Insulin-dependent diabetes mellitus (IDDM) is considered to be an autoimmune disease with destruction of beta cells in the islets of Langerhans mediated by immunocompetent cells. Islets of animals with spontaneously occurring IDDM (e.g., BB rats or NOD mice) have inflammatory cells that contain IL-1. Therefore, the inventive compounds should be useful for the prevention of and treatment of IDDM.

IL-1 also plays a role in the development of atherosclerosis. Endothelial cells are a target of IL-1. IL-1 stimulates proliferation of vascular smooth muscle cells. Foam cells isolated from fatty arterial plaques from hypercholesterolemic rabbits contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

In Vitro Assays for Physiologic and Pharmacologic Effects of the Inventive Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 µl complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thyroidine is added (for example, 1 µCi/well of 40 to 60 Ci/mmole) and proliferation determined by liquid scintillation counting.

A thymocyte costimulator assay is conducted to evaluate the inventive compounds to inhibit activation and proliferation of thymocytes caused by stimulation with Con A and interleukin-1 (IL-1), or interleukin-1 (IL-2). Thymuses are obtained from mice (e.g., female Balb/C mice) and the thymuses are removed and dissociated into culture media (e.g., RPMI 1640 without serum supplementation). The dissociated thymus tissue and cell suspension is transferred to centrifuge tubes and allowed to settle, washed with HBSS and resuspended in serum-supplemented culture media (e.g., RPMI 1640 with 10% fetal calf serum). Any contaminating red cells are lysed, and viable cells are resuspended and counted. Thymocytes are plated (e.g., 96-well plates at a density of $2\times10^5$ cells/well) and a stimulating agent, such as Con A, IL-1 (e.g., IL-1α) or IL-2 is added to the well. The cells are incubated for 4 days at 37° C. On the fourth day, the cells are pulsed with tritiated thymidine and cell proliferation determined. Inventive compounds are added at the time of stimulating agent addition.

Each inventive compound is investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microtiter plates and drug is added about two days after plating. Cell viability is determined using a fluorescent viability stain (e.g., 2',7'-bis-(2-carboroxyethyl)-5-(and -6)-carboxyfluorescein acetoxymethyl ester, BCECF excitation 488 nm and emission 525 nm) 24, 48 or 72 hours after addition of the drug.

Another assay for measuring activity of the inventive compounds involves determining PDGF (platelet derived growth factor) proliferative response using human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 µg/ml), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

Drug inhibitory activity can also be measured by determining levels of vascular cell adhesion molecule (VCAM) in stimulated cells. Early passage human umbilical vein endothelial cells (HUVEC) (obtained from commercial suppliers such as Cell Systems, Inc. or Clonetics) are cultured in media (e.g., Hepes buffered media, Cell Systems) containing 10% fetal bovine serum, and supplemented with a stimulating agent, such as fibroblast growth factor (acidic FGF, Cell Systems, Inc.) or TNF. The cells are plated into wells of a microtiter plate (e.g., $5\times10^4$ per well) and allowed to incubate at 37° C. for 72 hrs. The resting cells are removed (e.g., 20–30 min treatment with 0.4% EDTA), washed in media (e.g., phosphate buffered saline plus 0.1% bovine serum albumin with 0.01% sodium azide) and labeled on ice with a monoclonal antibody ("first antibody") recognizing human VCAM (e.g., 1 µg of a murine monoclonal antibody recognizing human VCAM, Genzyme). After 60 min on ice, the cells are washed (preferably twice) with cold wash media and incubated with an antibody that recognizes the first antibody (e.g., 1 µg of goat anti-mouse IgG conjugated with phycoerythrin, CalTag, Inc.). After 30 min on ice, the cells are washed twice and analyzed on a flow cytometer (Coulter Elite®) at appropriate emission and excitation wavelengths (e.g., for phycoerythrin use excitation at 488 nm and emission at 525 nm).

One in vitro assay measures inhibition of the relevant enzymes lysophosphatidic acid acyltransferase (LPAAT) and phosphatidic acid phosphoryl hydrolase (PAPH). The assay involves incubating of target cells with a primary stimulus (e.g., a variety of cytokines, growth factors, oncogene products, putative therapeutic agents, irradiation, viral infection, toxins, bacterial infection and the products thereof, and any stimulus which, if not counteracted, has a deleterious effect on the target cell) in the presence or absence of an inventive compound at varying dosage levels.

Target cells include, for example, subcellular entities, such as, microsomes derived from mesenchymal and/or ectodermal cells, particularly microsomes from marrow stroma cells or human or rat mesangial cells; microsomes or synaptosomes derived from brain; plasma membrane-enriched microsomes, plasma membranes derived as described in Bursten et al. (*J. Biol. Chem.* 226:20732–20743, 1991), or detergent-solubilized microsomes; synaptosomes, and membranes or other cell preparations solubilized using, for example, NP-40, Miranal, SDS or other neutral detergents; and detergent-solubilized, recombinant, or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, *Biochemistry* 30:6195–6203, 1991. A Rainin® mu-Porasil column is used with a 3:4 hexane:propanol organic carrier and a 1–10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

An inventive compound can be assayed for activity protecting TNF-mediated cytotoxicity. In this assay, L929 murine fibroblast cells ($10^4$ cells per well) are incubated with either compounds at varying doses and media control for two hrs. TNF-α (R&D Systems) is added at a concentration of 500 pg/ml, which is four times the LD50 of TNF (125 pg/ml). The cells plus (or minus) drug, plus TNF were incubated for 40 hrs at 37° C. The media is removed and replaced with fresh media containing 2% serum and 10 μg/ml of BCECF fluorescent dye and incubated for 30 min. The fluorescent dye-containing media is removed and replaced with PBS (phosphate buffered saline) and each well was assayed for fluorescence.

Another assay measures the effects of drug to inhibit adhesion of U937 cells to TNF-activated HUVEC cells In this experiment, HUVEC cells are induced with human TNF-α (20 ng/ml) and drug at varying concentrations for 14–16 hrs. U937 cells (a human monocyte cell line) are incubated and labeled with BCECF (10 μg/ml), a fluorescent dye. The U937 cell preparation ($2.5 \times 10^4$ cells per well) is layered on top of the activated HUVEC cells. The cells are reverse spun to remove partially adhering and nonadhering U937 cell. The adherent U937 cells are measured by fluorescence on a fluorescent plate reader.

Compounds of the Invention

The inventive compounds and pharmaceutical compositions are a resolved R or S (preferably R) enantiomer of an ω-1 alcohol of a straight chain alkyl ($C_{5-8}$) substituted at the 1-position of 3,7-disubstituted xanthine. The inventive compounds are effective in modulating cellular response to external or in situ primary stimuli, as well as to specific modes of administration of such compounds in effective amounts.

The inventive compounds comprise compounds and pharmaceutical compositions having a compound comprising a xanthine core of the formula:

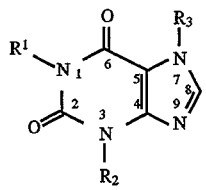

wherein $R_1$ is independently a resolved enantiomer cod secondary alcohol-substituted alkyl ($C_{5-8}$) substantially free of the other enantiomer, and wherein each of $R_2$ and $R_3$ is independently alkyl ($C_{1-12}$) optionally containing one or two nonadjacent oxygen atoms in place of a carbon atom. Preferably $R_1$ is a $C_6$ alkyl with the hydroxyl group as the R enantiomer.

The present invention further provides a pharmaceutical composition comprising an inventive compound and a pharmaceutically acceptable excipient, wherein the pharmaceutical composition is formulated for oral, parenteral or topical administration to a patient.

The present invention further comprises a pharmaceutical composition comprising one or a plurality of inventive compounds and a pharmaceutically acceptable carrier or excipient. The individuals to be treated with an inventive compound or inventive pharmaceutical composition may either be contacted with the compound of the invention in vitro culture, in an extracorporeal treatment, or by administering (oral, parenteral or topical) the compound of the invention or pharmaceutical composition to a subject whose cells are to be treated.

The (R) or (S) enantiomer of 1-(5-hydroxy-n-hexyl)-3,7-dimethylxanthine are known and prepared by conventional methods known in the art including microbial techniques, such as those described in Davis et al., *Xenobiotica*, 15:1001, 1985 and Davis et al., *Applied and Environmental Microbiology* 48:327, 1984, e.g., using *Rhodotorula rubra*, resolution of the racemate by formation of diastereomeric esters made with optically active acids such as (R) -alpha-methoxy-alpha-trifluormethyl-phenylacetic acid ((r)-MTFPA) and other optically active acids as in Davis et al (1984) supra, direct chemical synthesis by introducing the (R) or (S)-S-hydroxy-n-hexyl residue into the 1-position of the dimethylxanthine as described in European patent publication 0 435 153 and enantiomer selective conversion, e.g., wherein an enantiomeric ester is heated with a tertiary phosphine, an azodicarbonic acid dialkyl ester and a carboxylic acid, or an enantiomeric alcohol is converted into an organic sulfonic acid ester in an aprotic solvent optionally in the presence of base. The resulting aliphatic carbonic acid ester is heated to achieve solvolysis in the presence of base in an alcoholic or aqueous solvent (e.g., methanolysis in the presence of potassium carbonate) to obtain the enantiomeric alcohol as described in European patent publication 435 153 or 435 152.

Figure 9:
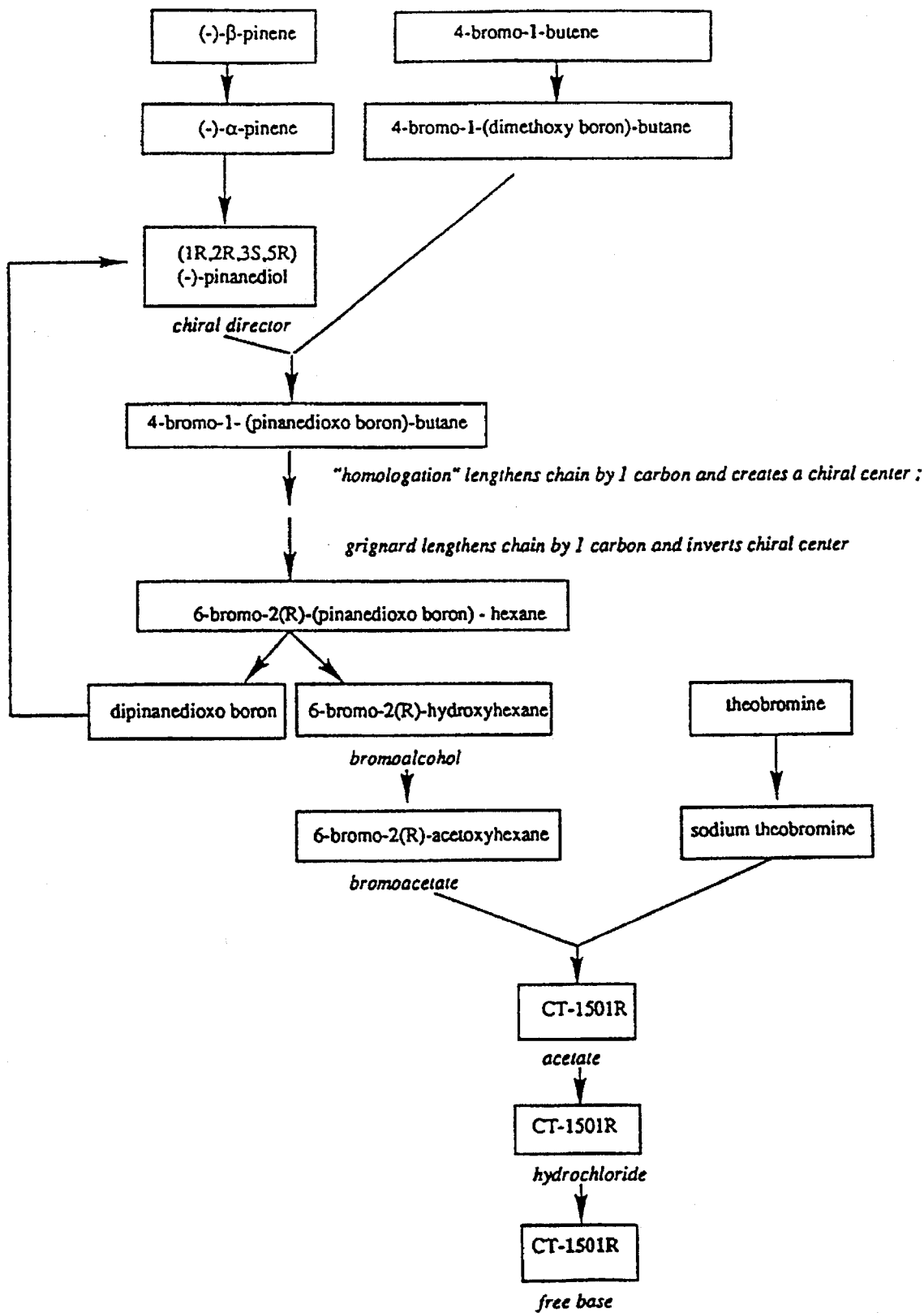
FIG. 9 shows a flow diagram of a large scale synthesis procedure for CT1501R.

A particularly preferred way of obtaining either the (R) or (S) enantiomer is a direct synthesis based on a modification of the method disclosed in *J. Org. Chem.* 55:2274, 1990 and shown as FIG. 9. In this method, 4-bromo-1-butene is heated with boron trichloride and triethylsilane in an inert hydrocarbon solvent such as pentane under low temperature conditions of about −10° C. to −78° C. to yield 4-bromo-1 (dichloro) borobutane. This product is then treated at about the same low temperature conditions with (R)- or (S)-pinanediol in an inert solvent such as diethyl ether or diglyme to give (R)- or (S)-pinanediol 4-bromobutylborate. This product is treated in an inert atmosphere such as argon with LiCHCl$_2$ at −100° C. (or somewhat warmer) in an inert solvent such as tetrahydrofuran followed by addition of anhydrous zinc chloride to yield (R)- or (S)-pinanediol 5-bromo-1-chlorpentylborate. This product is treated with methyl magnesium bromide at about −10° C. to about −78° C. in tetrahydrofuran to give R or S pinanediol 5-bromo-1-methylpentylborate. This product is treated with theobromine in dimethyl sulfoxide (DMSO) at about −10° C. to about 0° C. followed by distilling off the DMSO at about 28° C. and 5 torr to yield the corresponding 1-N-alkylated xanthine in very high yield of about 95%. The subsequent oxidative hydrolysis with a strong basic solution, such as excess aqueous sodium hydroxide, removes the boron atom and (R)- or (S)-pinanediol residue. The products are obtained by conventional recovery methods such as recrystallization from a solvent like isopropanol. The following also illustrates this preferred synthesis method.

Outline of the synthesis of CT-1501R from "bromoacetate" and theobromine:

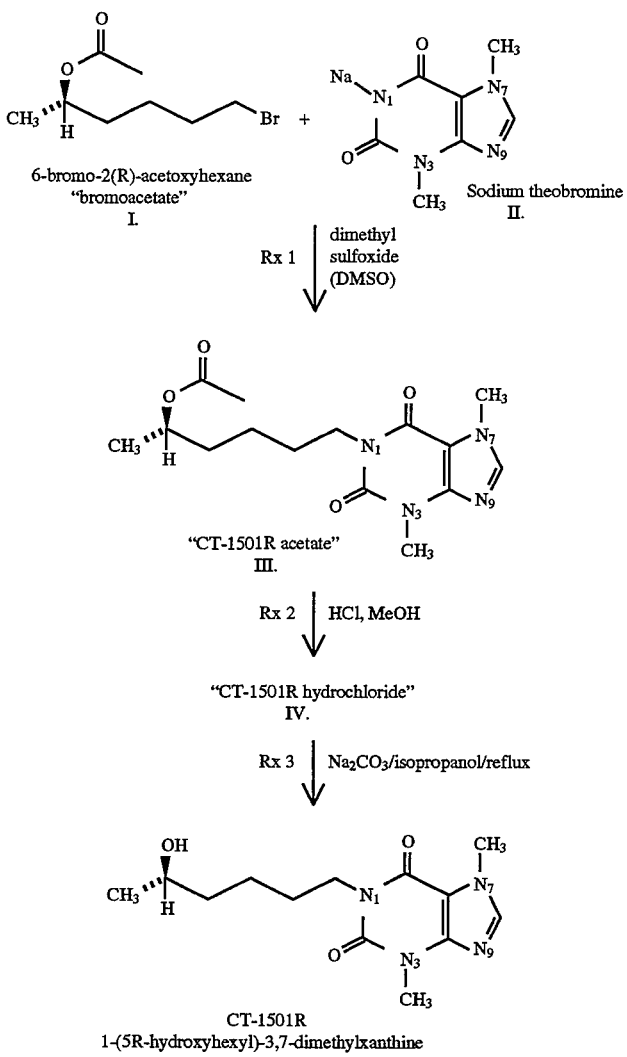

Outline of the synthesis of sodium theobromine (II):

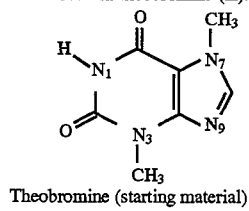

-continued
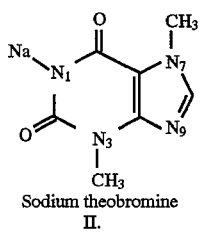
Sodium theobromine
II.
Outline of the synthesis of bromoacetate (I):
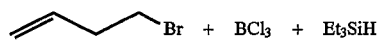
4-bromo-1-butene
(starting material)
Rx 5 | hexane
↓
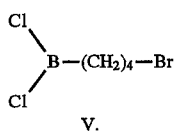
V.
V. + methanol
Rx 6 | methanol
↓
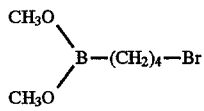
4-bromo-1-(dimethoxyboron)-butane
VI.
Rx 7
tetrahydrofuran
(THF)
(1R,2R,3S,5R)-(−)-pinanediol (chiral director)
↓
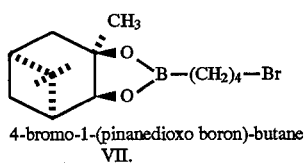
4-bromo-1-(pinanedioxo boron)-butane
VII.

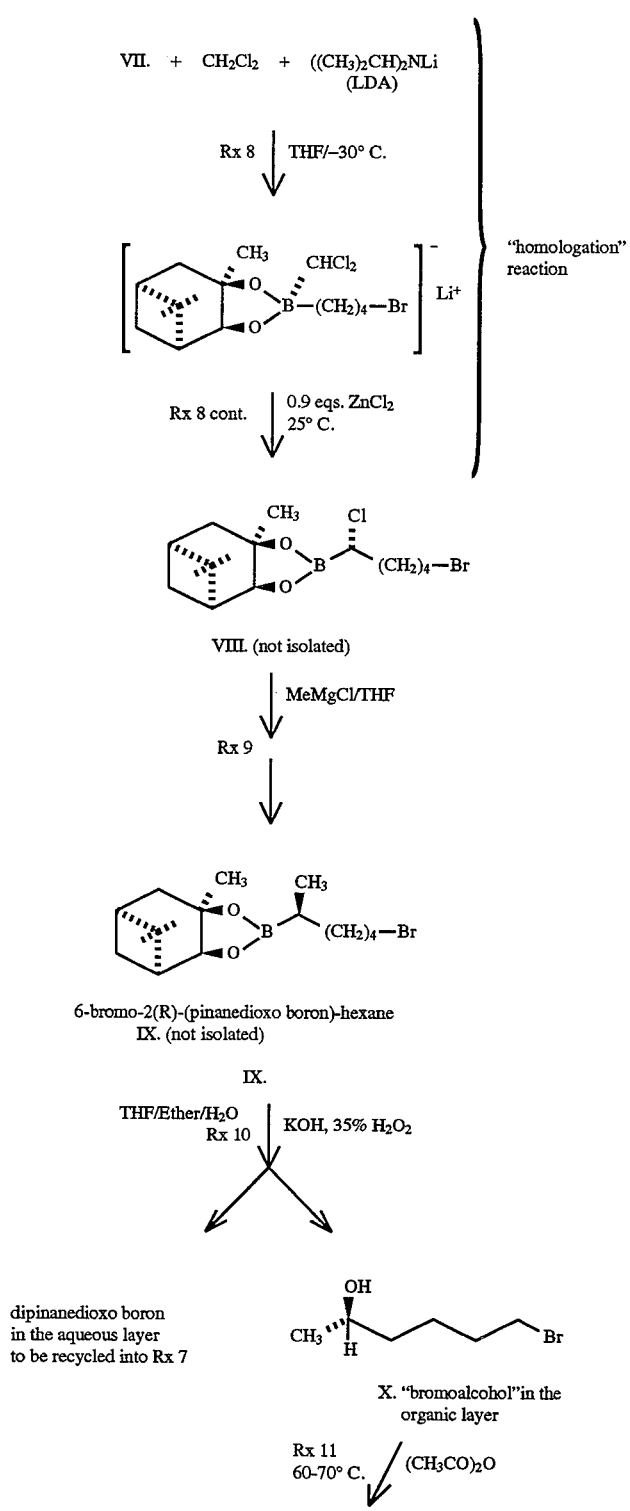

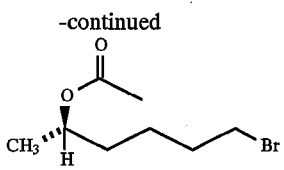

I. "bromoacetate"

purified by distillation at 0.7 mm, head temperature of 60° C.

For reference with respect to reactions 5 thru 9 see:
J. Am,Chem,Soc. Vol.108, No.4, 1986,
Matteson, Sadhu & Peterson.

Pinanediol is the chiral director used in the preferred synthesis method, Pinanediol can be synthesized according to the following synthesis procedure.

Outline of the synthesis of pinanediol (chiral director):

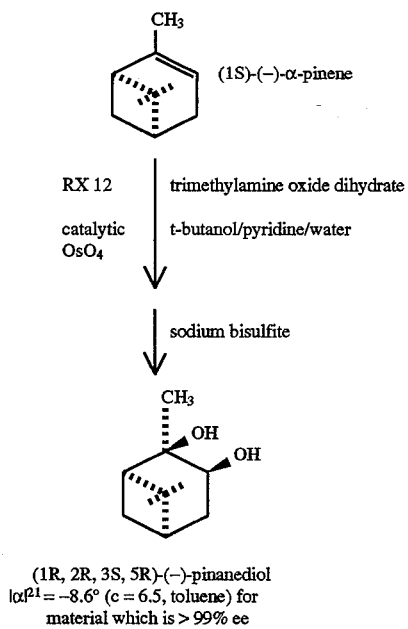

(1R, 2R, 3S, 5R)-(−)-pinanediol
$[\alpha]^{21} = -8.6°$ (c = 6.5, toluene) for material which is > 99% ee The synthesis procedure utilizes -(−)-α-pinene, which is often not available in commercial scale quantities. However, -(−)-α-pinene can be made from-(−)-β-pinene according to the following procedure.

Outline of α-pinene synthesis:

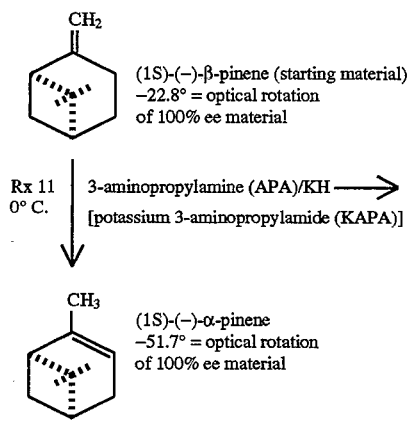

It is also important to regenerate pinanediol from reaction 10 to recycle this valuable starting material and chiral director to use repeatedly in many reactions. A preferred recycling method to regenerate pinanediol is illustrated as follows:

Recovery of pinanediol from Rx 10 for recycling into Rx 7:

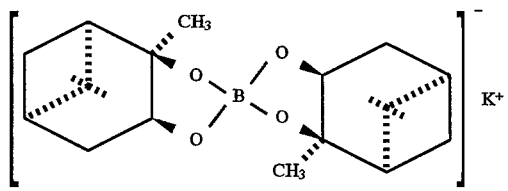

dipinanediol boron,
the form in which pinanediol is released from reaction 10

Rx 13 | diethylether/water
4 equivalents HF

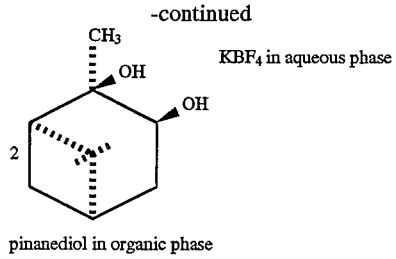

pinanediol in organic phase

Uses of the Invention Compounds and Pharmaceutical Formulations

The compounds of the invention provide a mechanism to maintain homeostasis in cells contacted by primary stimuli through mitigating the effects of these primary stimuli on the secondary signaling pathways invoked within seconds of the primary stimulus. For example, administration of the inventive compounds in vivo or ex vivo provide a method to modify cellular behavior which method comprises contacting cells (in vivo or ex vivo) whose behavior is to be modified with an effective amount of an inventive compound or a pharmaceutical composition thereof wherein said method is: (1) a method to inhibit proliferation of tumor cells and said amount is sufficient to inhibit said proliferation; or (2) a method to promote differentiation of hematopoietic stem cells into red blood cells, platelets, lymphocytes, and granulocytes, and said amount is sufficient to promote said proliferation; or (3) a method to suppress activation of T-cells by antigen or IL-2 stimulation, and said amount is sufficient to promote said activation; or (4) a method to suppress activation of monocyte/macrophage cells by endotoxin, TNF, IL-1 or GM-CSF stimulation and said amount is sufficient to suppress said activation; or (5) a method to enhance the resistance of mesenchymal cells to the cytotoxic effect of tumor necrosis factor and said amount is sufficient to enhance said resistance; or (6) a method to suppress antibody production of β-cells in response to an antigen, IL-4 or CD40 ligand and said amount is sufficient to suppress said antibody production; or (7) a method to inhibit the proliferation of smooth muscle cells in response to growth factors capable of stimulating said proliferation and said amount is sufficient to inhibit said proliferation; or (8) a method to lower systemic vascular resistance conferred by endothelial cells and said amount is sufficient to reduce the release of hypertension-inducing substances; or (9) a method to lower systemic vascular resistance induced by endothelial cells and said amount is sufficient to enhance the release of anti-hypertensive substances; or (10) a method to lower expression of adhesion molecules induced by enhancers thereof, and said amount is sufficient to lower said expression; or (11) a method to suppress the activation of T-cells by HIV and said amount is sufficient to suppress said activation thus inhibiting viral replication; or (12) a method to inhibit the proliferation of kidney mesangial cells in response to stimulation by IL-1 and/or mip-α and/or PDGF and/or FGF and said amount is sufficient to inhibit said proliferation; or (13) a method to enhance the resistance of kidney glomerular or tubular cells to cyclosporin A or amphotericin B and said amount is sufficient to enhance said resistance; or (14) a method to prevent the suppression of growth stimulatory factor production in TNF-treated bone marrow stromal cells and said amount is sufficient to prevent said suppression; or (15) a method to prevent the release of mip-1α by IL-1, TNF, or endotoxin stimulated monocytes and macrophages; or (16) a method to prevent the release of platelet activating factor by IL-1, TNF, or endotoxin treated megakaryocytes, fibroblastic cells, find macrophages; or (17) a method to prevent the down-regulator of receptors for cytokines in TNF-treated hematopoietic progenitor cells and said amount is sufficient to prevent said down-regulation; or (18) a method to suppress the production of metalloproteases in IL-1-stimulated or TNF-stimulated glomerular epithelial cells or synovial cells and said amount is sufficient to enhance said production; or (19) a method to enhance the resistance of gastrointestinal or pulmonary epithelial cells to cytotoxic drugs or radiation and said amount is sufficient to enhance said resistance; or (20) a method to enhance the antitumor effect of a non-alkylating antitumor agent and said amount is sufficient to enhance said effect, or (21) a method to inhibit the production of osteoclast activating factor in response to IL-1, and said amount is sufficient to inhibit said production, or (22) a method to inhibit degranulation in response to IgE, and said amount is sufficient to inhibit said degranulation, or (23) a method to enhance the release of adrenergic neural transmitters, dopamine, norepinephrine, or epinephrine, or the neurotransmitter, acetylcholine, and said amount is sufficient to enhance said release, or (24) a method to modulate the post-synaptic "slow current" effects of the adrenergic neurotransmitters dopamine, epinephrine, or norepinephrine, or the neurotransmitter acetylcholine, and said amount is sufficient to modulate such slow currents.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7–10 consecutive days before the new or stored bone marrow is infused. The day on which the marrow is given to the patient is referred to as day 0 of the transplant. Previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. Inventive Compounds are able to increase the percentage of patients who survive. The percentage of fatalities within the first 100 days that is considered acceptable is 15–20% for "good risk" patients and 30–40% for "high risk". These fatalities are due to the direct effects of high doses of chemo/radiation. In addition, GVHD contributes to the death rate in allogeneic marrow recipients.

Other indications for which it is useful to administer the compounds of the invention include the presence of a tumor burden, a hormone-related disorder, a neurological disorder, an autoimmune disease, inflammation, restenosis, coronary artery disease, atherosclerosis, hypertension, unwanted immune response, viral infection, nephritis, mucositis, and various allergic responses. Prevention of allergic responses include prevention of acute allergic response and thus moderation or prevention of rhinorrhea, sinus drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV1, changes in vital capacity, and extensive mucus production.

Other suitable subjects for the administration of compounds of the invention, include patients being administered cytoreductive agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progessive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiring such treatment as an effective oral, parenteral, or intravenous 'sublethal dose of about 200 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Coadministration With a P-450 Inhibitor

The coadministration in vivo of the compounds of the invention along with an inhibitor of P-450 results in an enhanced effect due to a longer half life of the inventive compounds. This in vivo effect is due to inhibition of a degradation pathway for the compounds of the invention; in particular, dealkylation at the N7 position of the xanthine ring. For example, NIH3T3-D5C3 cells can be used to compare effects of an inventive compound alone or in combination with a P-450 inhibitor by comparing transformation phenotype control, incubation with an inventive compound alone, and coincubation of an inventive compound with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

Depending on the inventive compound selected, the level of dosage can be appreciably diminished by coadministration of a P-450 inhibitor, such as the quinolone. Alternatively, a strong synergistic effect may be obtained with such a quinolone.

The invention is illustrated by the following examples which should not be regarded as limiting the invention in any way. In these examples PTX means pentoxifylline.

EXAMPLE 1

This example illustrates a synthesis for CT1501R by resolution of racemic M1. To ether saturated with M1 in a reaction vial was added 3.0 equivalent of pyridine (freshly distilled from calcium hydride) and 3 equivalents of the acid chloride of R-(+)-1-methoxy-1-trifluoromethyl-phenylacetic acid ((+)-MTFPA). The reaction vial was sealed, 30 warmed at fifty degrees C. for 1 hour, placed under a stream of nitrogen until dry, and then reconstituted in 75% MeOH/H$_2$O. Separation was achieved using an isocratic system of 90% (75% MeOH/water), 3% acetonitrile (AcN), 7% water at a flow rate of 3.0 ml/min through a 250×10 mm Ultremex 5 C-18 column (Phenomenex, Torrance, Calif. 90501). Samples were prepared as 10% solutions of MTFPA-M1 in 75% MeOH/water, 100 µl aliquots were injected every 7 min for 21 min (4 injections). Compounds were eluted at 29.8 min (S-M1)-MTFPA, and 31.4 min (R-M1)-MTFPA with 95% separation. Assignment of absolute configuration was based on NMR, as described by Dale et at. (*J. Org. Chem.* 34:2543, 1969). Collected fractions were combined and reduced in volume with a rotovap. Initially, samples were evaporated only to remove MeOH and AcN after which they were extracted with chloroform. The solvent was dried and removed in vacuo. Later, the extraction step was omitted after studies showed that the ester was stable to the minor elevation of temperature required to remove water.

Hydrolysis of (+)-MTFPA-M1 Stereoisomers

For monitoring the progress of hydrolysis of MTFPA esters, it was necessary to develop an assay that would quantitate M1 directly as well as the total ester present. A gradient program was used changing the mobile phase from 40% (75% MeOH/water) 10% AcN 50% water to 40% (75% MeOH/water) 60% AcN from 1.0–8.0 min after injection. The final conditions were maintained for 3 min after which the column was reequilibrated to starting conditions. Eluent was monitored at 280 nm and retention times were 6.5 min and 12.3 min for free and derivatized M1, respectively. Using this system there was no separation of stereoisomers of derivatized M1 and so it could be used as an assay for monitoring of hydrolysis of MTFPA esters.

To 30 mg of pure MTFPA-M1 ester (R or S derivative) in 4.0 ml EtOH was added ca. 40 mg sodium borohydride (NaBH) and this mixture was heated in an oil bath to 70° C. Additional sodium borohydride (20 mg) was added every 4 hours during the day. After 54 hours the reaction was approximately 90% complete (via HPLC) with no loss of the total peak area of M1+M1-ester. The reaction was terminated with monobasic sodium phosphate/water, adjusted to pH 3.5 with HCl, the EtOH was removed in vacuo, and unreacted ester and M1 extracted into chloroform. The chloroform was dried over sodium sulfate and removed in vacuo. The crude product was purified using preparative chromatography with the solvent gradient outlined above for M1 using a flow rate of 3.0 ml/min with the 250×10 mm column. Collected fractions were reduced to dryness in vacuo, triturated with ether, and analyzed for enantiomeric excess (>95% for both isomers). Ether was removed under nitrogen and the resulting crystals dissolved in a minimal volume of normal saline. Dilutions were made of this standardized solution with normal saline to produce 10 mM solutions of each enantiomer. Enantiomeric identity was confirmed by HPLC of reformed MTFPA esters.

EXAMPLE 2

This example illustrates a process for preparing (R) 1-(5-hydroxyhexyl)-3,7-dimethylxanthine) (CT1501R) using R pinanediol as a chiral director on a laboratory scale. Triethylsilane (83.49 g, 0.718 moles) and 4-bromo-1-butene (97 g, 0.718 moles) were mixed in a 500 ml round bottomed flask and cooled to −78° C. In a one liter round bottomed flask, boron trichloride (84.13 g, 0.718 moles) gas was condensed at −78° C. and 400 ml of pentane were added. The silane/butene mixture was added to the boron trichloride solution dropwise via a canula with stirring, under argon, while maintaining an internal temperature of −78° C. When the addition was completed, three equivalents of methanol were added dropwise to the. The solution was then warmed to room temperature, and the pentane, HCl, and excess methanol were distilled off under argon at atmospheric pressure. The residue was vacuum distilled to give dimethyl 4-bromobutyl boronate; (bp 70°–79° C. at 0.9 torr, yield 127.5 g, 85% yield).

In a 500 ml round bottomed flask, (R)-pinanediol (62 g; 0.365 moles) and dimethyl 4-bromobutylboronate (75 g; 0.359 moles) were stirred with 200 ml of diethyl ether. After 30 min the ether was removed under vacuum and the residue was distilled to yield (R)-pinanediol-4-bromobutyl boronate; (bp 134°–141° C. at 1.6–1.9 torr, 110.85 g, 98% yield).

To perform the homologation reaction, methylene chloride (31.47 g; 0.370 moles) and 500 ml of anhydrous THF were cooled to −100° C. under argon with stirring in a one liter round bottomed flask with a side arm. To the cooled solution, 212 ml of n-butyllithium (1.4N in hexanes) were added dropwise down the side of the flask over 45 min with stirring under argon while maintaining the internal temperature at −100° C. The solution was allowed to stir 20 min after addition was complete. Pinanediol 4-bromobutylboronate (77.82 g; 0.247 moles) was mixed with 100 ml anhydrous THF, cooled to −78° C., and then added to the lithium methyl dichloride solution dropwise while keeping the internal temperature at 100° C. Upon completion of the addition, rigorously dried zinc chloride (30.29 g; 0.222 moles) was added. The solution was stirred under argon for 10 hr and warmed to room temperature. The solvents were removed under vacuum. To the residue was added 500 ml petroleum ether and 300 ml saturated aqueous ammonium chloride. The organic phase was separated and washed with saturated ammonium chloride (2×250 ml). The aqueous phases were combined and washed with petroleum ether (2×250 ml). The organic phases were combined and dried with sodium sulfate, filtered and evaporated to give crude pinanediol (R) bromopentylboronate, crude wt. 92.13 g (102%).

In a 500 ml round bottomed flask, 300 ml of anhydrous THF and the crude pinanediol (R)-1-chloro-5-bromopentylboronate from the previous reaction (assuming 89 g; 0.247 moles) were mixed and cooled to −78° C. with Stirring under argon. To the solution was added methylmagnesium bromide (3.26N, 79.6 ml). The solution was warmed to room temperature overnight. Petroleum ether (500 ml) and saturated ammonium chloride (250 ml) were added, forming an emulsion. The aqueous phases were separated. The organic phase was washed with saturated ammonium chloride (2×250 ml), causing the emulsion to disappear. The combined aqueous phases were washed with petroleum ether (2×250 ml). The combined organic phases were dried over sodium sulfate, filtered and evaporated under vacuum to yield 85.85 g of crude pinanediol (R)-5-bromo-1-methylpentylboronate.

In a 5 liter flask, 2 liters of DMSO and theobromine (44.51 g, 0.247 moles) were combined with stirring under argon. Sodium hydride (9.9 g; 0.247 moles) was added in two aliquots to the solution and allowed to stir until the theobromine was dissolved. After 3 hr, the pinanediol (R)-5-bromo-1-methylpentylboronate from the previous reaction (84.75 g; 0.247 moles) was added neat to the solution dropwise and allowed to stir for 12 hr.

The DMSO was distilled from the solution (it may be recycled). The residue was treated with 500 ml of methylene chloride and 500 ml water. The aqueous phase was removed and the organic phase was washed (3×750 ml) with water. The aqueous phases were combined and extracted with 2×500 ml of methylene chloride. The organic phases were combined, dried with sodium sulfate, filtered and the solvents removed under vacuum to yield 88.14 g, 80% yield) of pinanediol (R)-5-(3,7-dimethylxanthine)-1-methylpentyl boronate.

The boronate was then dissolved in THF/water (300 ml each) and the mixture cooled to 0° C. with stirring under argon. While maintaining the internal temperature at 0° C., 95 ml of 3N potassium hydroxide was added dropwise followed by dropwise addition of 32.3 ml of 30% hydrogen peroxide. The mixture was stirred for 2 hr and the solids were filtered off. Water and methylene chloride (300 ml each) were added. The phases were separated and the aqueous phase was washed 4×100 ml with methylene chloride. The combined organic phases were dried over sodium sulfate, filtered and evaporated. The residue was recrystallized with a minimal amount of methylene chloride and a larger amount of ether. The yield was 46.3 g (87%) of (R)-1-(5-hydroxyhexyl)-3,7-dimethyl xanthine m.p. 105°–108° C., $[\alpha]D=-5.63$, ca. 96% ee.

EXAMPLE 3

This example illustrates a process for preparing of (R)-1-(5-hydroxyhexyl)-3,7-dimethylxanthine (CT1501R) using DICHED as a chiral director: The pinanediol chiral director described in example 2 can be replaced with (1S,2S)-(1,2)-dicyclohexylethanediol (DICHED). This chiral director is more easily recovered (95%) than the pinanediol. DICHED can be prepared according to a procedure described in Sharpless et at., *J. Org. Chem.* 57:2768, 1992. Dimethyl-4-bromobutylboronate (10.1 g, 48.06 mmol), prepared as described above was mixed with 10.54 g (46.6 mmol) of (S,S)-DICHED in 100 ml of ether. After 30 min, the ether was removed and the residue put through a short column of 10 g of silica gel and eluted with petroleum ether/ether (9:1), yielding 17.8 g of the (S,S) DICHED analog 4-bromobutylboronate.

The homologation reaction was performed as described in example 2 with the following amounts: 17.8 g of DICHED 4-bromobutylboronate; 6.11 g of methylene chloride; 41.2 ml of 1.4N n-butyllithium; 100 ml of THF and 5.89 g of anhydrous zinc chloride.

The Grignard reaction was performed, as in example 2, with the following amounts: DICHED (R)-1-chloro-5-bromopentylboronate, 20.04 g; 3.0N methylmagnesium bromide, 16.7 ml; 150 ml of THF. The oxidation of the DICHED boronate to give (R)-6-bromohexan-2-ol was performed by dissolving the DICHED 5-bromo-1-methylpentylboronate in THF (10 ml) in a 50 ml flask. Water (10 ml) was added and the solution. The solution was cooled to 0° C. while stirring under argon. Sodium carbonate (16.5 ml of a 3M solution) was added, followed by 8 ml of 30% hydrogen peroxide. The solution was filtered, 20 ml of pentane added, and filtered again. The aqueous phase was separated and washed with pentane (2×10 ml). The organic phase was dried over sodium sulfate, filtered and the solvent evaporated to give (R)-6-bromo-hexan-2-ol in a crude yield of 8.9 g. Vacuum distillation provided a yield of 7.1 g (84%) of pure material with a rotation of $-13.89$ $[\alpha]_{549}$.

The (R)-bromoalcohol was added to theobromine. A mixture of theobromine (2.02 g, 11.2 mmol) was stirred in DMSO (30 ml), and 282 mg of sodium hydride (11.8 mmol) was added. The reaction mixture was vigorously stirred for 80 minutes. The bromoalcohol (2.03 g, 11.2 mmol) was added dropwise and the stirring continued for 21 hr. DMSO was distilled off under full pump vacuum. Water (100 ml) was added. The mixture was extracted with 25% ethanol/methylene chloride (3×50 ml) and the combined extracts were dried over magnesium sulfate and evaporated. The residue was taken up in 20 ml of methylene chloride and 150 ml of ether was added. Beige crystals formed of (R)-1-(5-hydroxyhexyl)-3,7dimethylxanthine (1.5 g, 5.36 mmol, 47.8% yield). Another 500 mg of the product crystallized over the next 24 hr to give a total yield of 2 g (64% overall) with greater than 94% ee by chiral chromatography.

EXAMPLE 4

This example illustrates a process for synthesis of (R or S)-1-(6-hydroxyheptyl)-3,7-dimethyl-10 xanthine or (R or S)-7-hydroxyoctyl)-3.7-dimethylxanthine. These compounds were prepared using the appropriate pinanediol and DICHED procedures described above by using as starting materials the longer chain bromoolefins, 5-bromo-1-pentene and 6-bromo-1-hexene,15 respectively.

EXAMPLE 5

This example illustrates a mixed lymphocyte reaction of CT1501R and PTX. The mixed lymphocyte reaction shows a proliferative response of PBMC (peripheral blood mononuclear cells) to allogeneic stimulation determined in a two-way mixed lymphocyte reaction. Both CT1501R and PTX showed activity in this immune modulating activity assay procedure as shown in FIG. 1.

EXAMPLE 6

Figure 2:
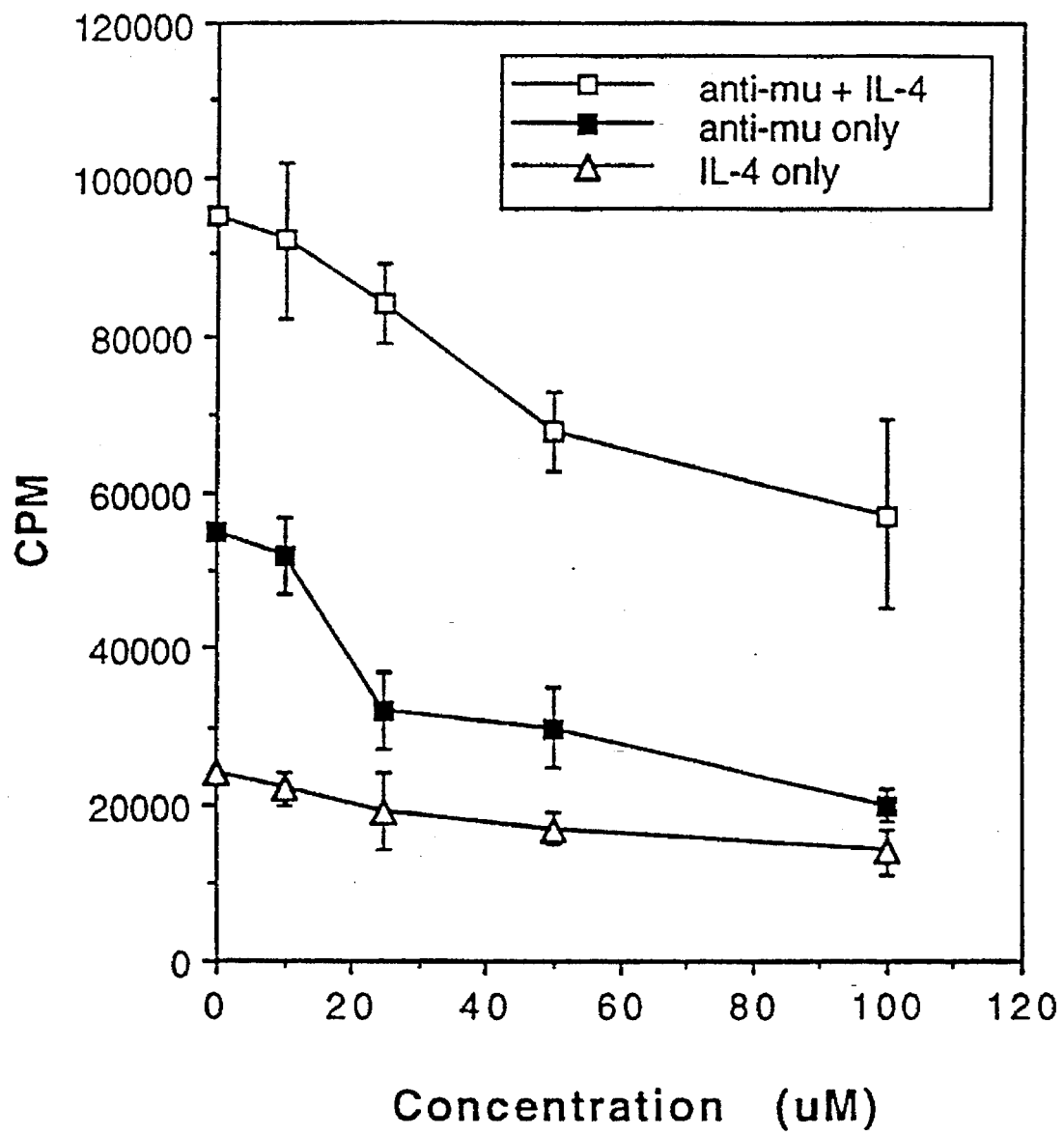
FIG. 2 shows the effects of CT1501R on inhibition of murine B-cell proliferation stimulated by anti-mu antibody crosslinked and/or interleukin-4 (IL-4).

This example shows the effects of CT1501R on inhibition of murine B-cell proliferation stimulated by anti-mu antibody crosslinked and/or interleukin-4 (IL-4). FIG. 2 shows that CT1501R inhibited B-cell proliferation caused by the indicated proliferative signals.

Figure 3:
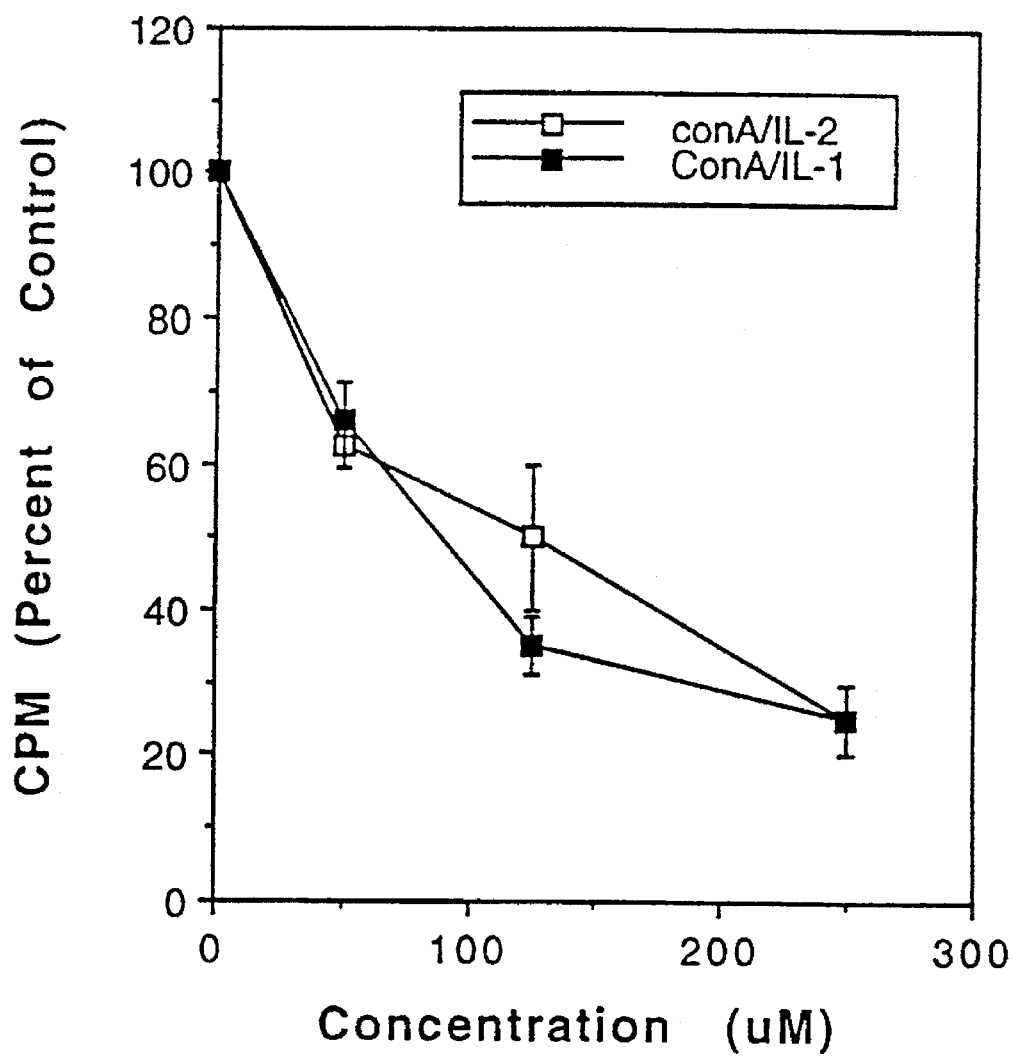
FIG. 3 shows the effects of CT1501R inhibiting proliferation caused by Concanavalin A (ConA) and interleukin-1 alpha (IL-1$\alpha$) or interleukin-2 (IL-2). CT1501R was added to the cells at the doses indicated two hours prior to activation with ConA and IL-1$\alpha$ or IL-2. CT1501R inhibited thymocyte proliferation in a dose-response manner as is shown in FIG. 3. Background counts were less than 200 cpm.

FIG. 3 shows the effects of CT1501R inhibiting proliferation caused by Concanavalin A (ConA) and interleukin-1 alpha (IL-1α) or interleukin-2 (IL-2). CT1501R was added to the cells at the doses indicated two hours prior to activation with ConA and IL-1α or IL-2. CT1501R inhibited thymocyte proliferation in a dose-response manner as is shown in FIG. 3. Background counts were less than 200 cpm.

Figure 4:
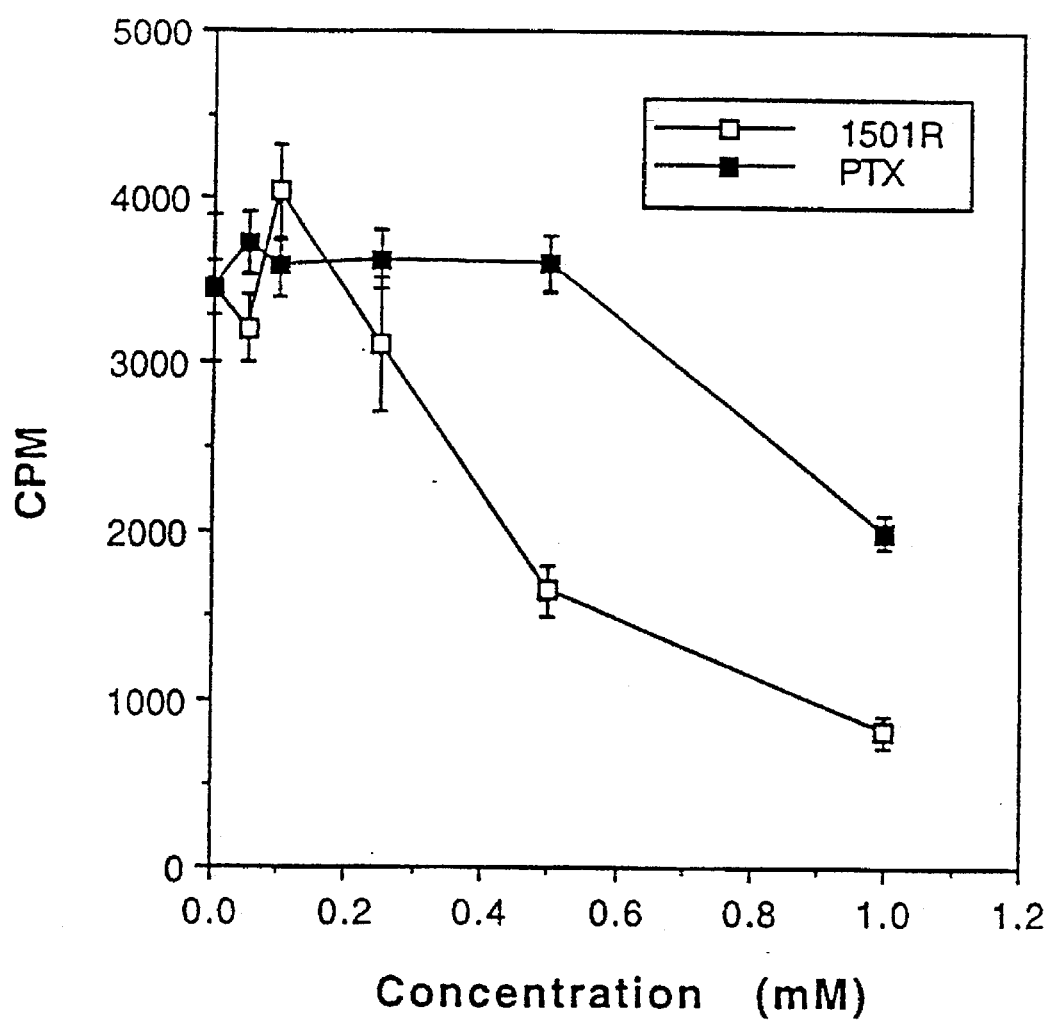
FIG. 4 shows the effects of CT1501R and PTX on inhibition of smooth muscle proliferation stimulated by PDGF (platelet derived growth factor) and IL-1. CT1501R and PTX were separately added to the cells two hours prior to activation with PDGF and IL-1. Both drugs inhibited smooth muscle cell proliferation at the higher doses tested as shown in FIG. 4. CT1501R was more active than PTX.

FIG. 4 shows the effects of CT1501R and PTX on inhibition of smooth muscle proliferation stimulated by PDGF (platelet derived growth factor) and IL-1. CT1501R and PTX were separately added to the cells two hours prior to activation with PDGF and IL-1. Both drugs inhibited smooth muscle cell proliferation at the higher doses tested as shown in FIG. 4 with CT1501R being more active than PTX.

EXAMPLE 7

This example illustrates in vitro effects of CT1501R, including inhibition of cytokine release and cellular adhesion. We determined the effects of CT1501R on endotoxin, TNF-α or IL-1α-stimulated cytokine release and adhesion to activated human umbilical endothelial cells.

Murine peritoneal exudate cell macrophages (PEC) were isolated by perfusion of mouse peritoneum and plated into 96-well trays at $5\times10^5$ cells per well. Cells were stimulated with 5 μg/ml *Salmonella abortus* equi-derived endotoxin (LPS; Sigma Chemical Co., L-1887) or 50 ng/ml IL-1α (Genzyme; Cambridge, Mass.) with or without the addition of CT1501R added to the cultures one hour prior to addition of the stimulus. At various times thereafter, supernatants were removed and levels of either TNF-α or IL-1α were assayed using commercial 96-well microtiter immunoassay kits (Genzyme; TNF; Endogen, Boston, Mass.; IL-1α) according to manufacturer's specifications. For the adhesion studies, early passage human umbilical vein endothelial cells (HUVEC) were obtained from commercial suppliers (Clonetics, San Diego, Calif. or Cell Systems, Seattle, Wash.) and cultured in defined, Hepes buffered, serum free medium (Cell Systems, cat 301-180) supplemented with acidic FGF (Cell Systems cat 401-111). 4000 cells were plated into each well of a 96 -well microtiter plate and allowed to incubate for 72 hrs at 37° C. The histiocytic leukemia cell line U937 was stimulated in RPMI 1640 medium supplemented with 10% fetal calf serum. Either the HUVEC or U937 cells were stimulated with either LPS, IL-1α or TNF-α for 12 hrs. For the adhesion assay, U937 cells were labeled with the fluorescent viability stain, 2',7'-bis-(2-carboxyethyl)-5-(and-6)-carboxyfluorescein acetoxymethyl ester (BCECF). Briefly, the cells were labeled with 10 μg/ml BCECF in RPMI-1640 media plus 10% fetal calf serum for 30 min at 37° C. The cells were washed once with full media and 50,000 cells/well added to the HUVEC cultures. The samples were incubated at 37° C. for 30 min, inverted and centrifuged for 10 min at 400×g. After addition of 100 ml Hanks Balanced Salt Solution (HBSS), the microtiter plate was then analyzed on a Millipore Cytofluor fluorescent plate reader (excitation 488 nm; emission 525 nm). Fluorescence of serial dilutions of cells showed a linear concentration relationship over wide ranges of cell concentrations from 20 to 100,000 cells per well (data not shown). All experiments were repeated at least in duplicate with all results confirming the findings of those shown.

Figure 18:
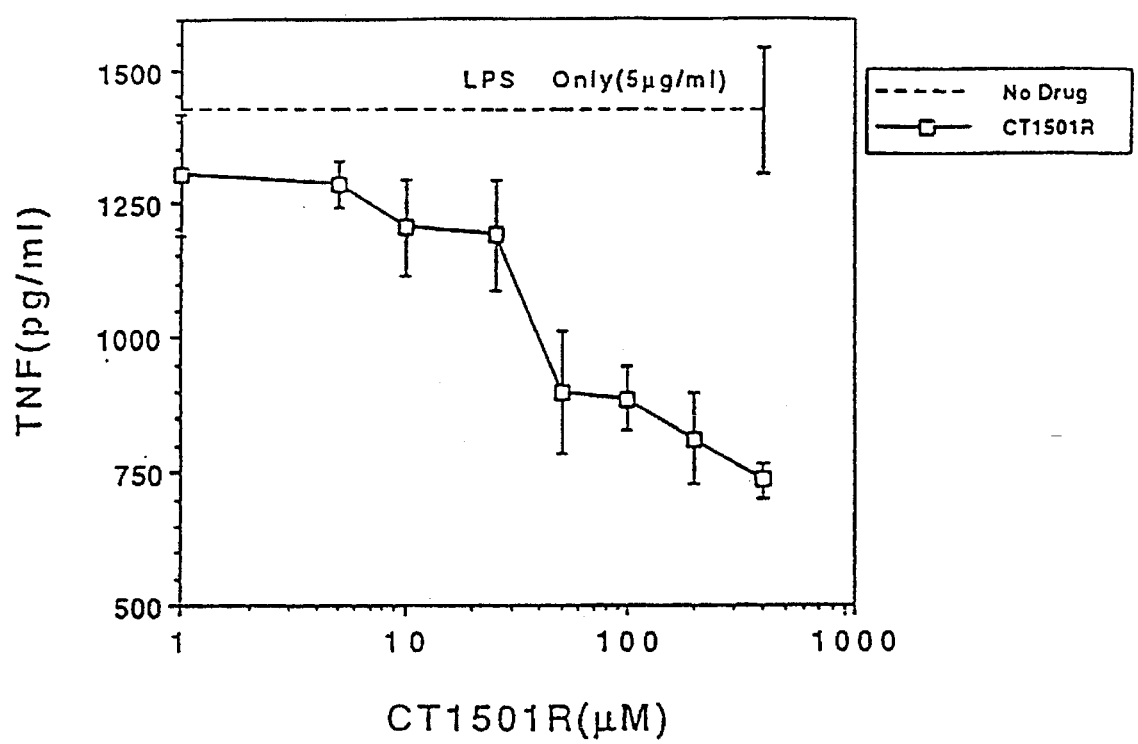
FIG. 18 shows a dose response for inhibition of TNF-α release from LPS-activated mouse peritoneal macrophages by CT1501R. Cells were isolated and treated with or without various concentrations of CT1501R one hour prior to LPS activation (10 mg/ml). Twenty four hours later the supernatants were collected assayed for TNF-α by ELISA (+/–SD).

CT1501R inhibited TNF-α release from LPS stimulated PEC cells. Cells were pretreated with 250 mM CT1501R and supernatants assayed by ELISA for released TNF-α as a function of time following LPS stimulation. CT1501R significantly inhibited TNF-α release at all time points measured from approximately 50% of LPS induced levels at 6–24 hrs to approximately 70% at 48 hr. A dose response of the effects of CT1501R on released TNF is shown in FIG. 18. PEC cells were stimulated with LPS 1 hour following treatment with various concentrations of CT1501R. The concentration for CT1501R 50% inhibition was approximately 30 μM. At 500 μM the inhibitory effects of CT1501R were approximately 40% of the maximal LPS stimulation (1428 pg/ml).

Figure 19:
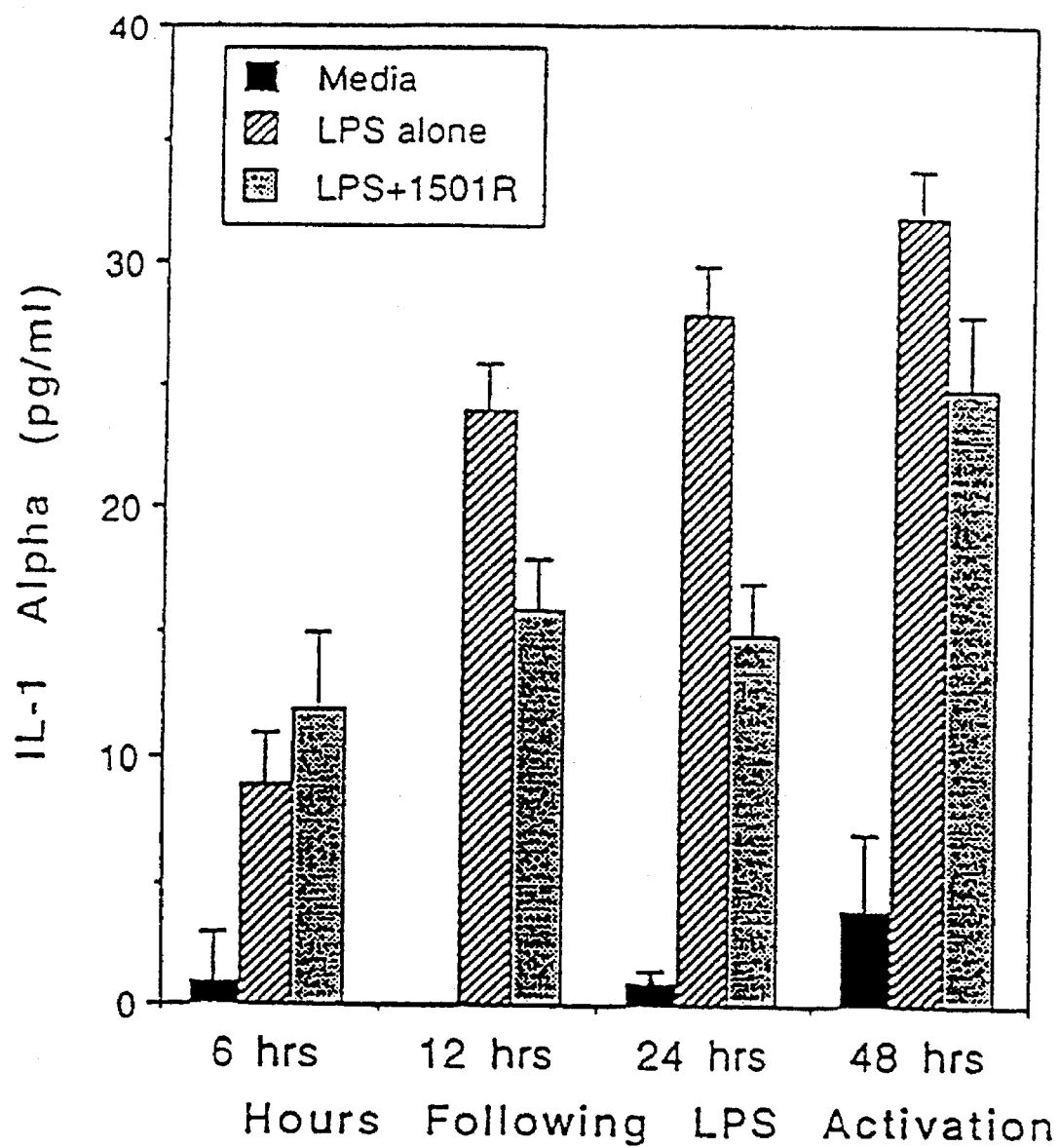
FIG. 19 shows inhibition of IL-1-α release in LPS activated PEC by CT1501R. Cells were isolated and treated with or without 250 µM CT1501R one hour prior to activation with 10 µg/ml LPS. At various times later, supernatants were harvested and assayed for IL-1-α by ELISA (+/–SD)
Figure 20:
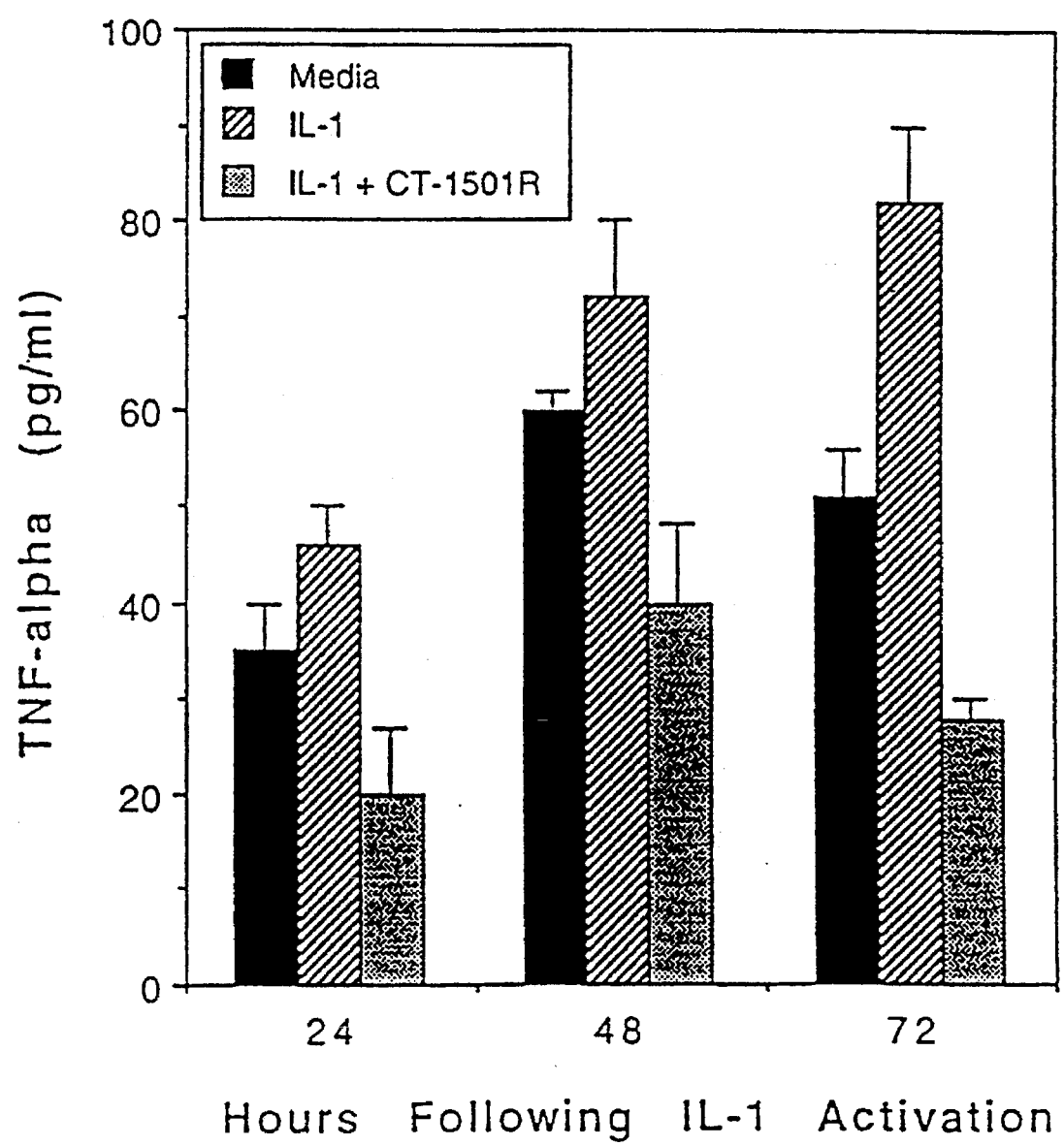
FIG. 20 shows inhibition of TNF-α release from IL-1-α-activated mouse peritoneal macrophages. Cells were isolated and treated with or without CT1501R (250 µM) 1 hour prior to IL-1-α activation. The supernatants were collected at 24, 48 or 72 hrs following activation and assayed for TNF-α by ELISA (+/–SD).

LPS stimulates IL-1α release in peritoneal macrophages, increasing to levels of 24 pg/ml by 12 hours following LPS stimulation, and 31 pg/ml by 48 hrs (FIG. 19). Addition of CT1501R significantly attenuated IL-1α release at 12–48 hrs, with a maximum inhibition of approximately 50% at 24 hours. If the peritoneal macrophages were stimulated with 50 ng/ml IL-1α rather than LPS (FIG. 20), CT1501R also inhibited release of TNF-α (FIG. 20). Addition of CT1501R resulted in a 50%–70% inhibition of induced levels of TNF-α at the tested time points.

Figure 21:
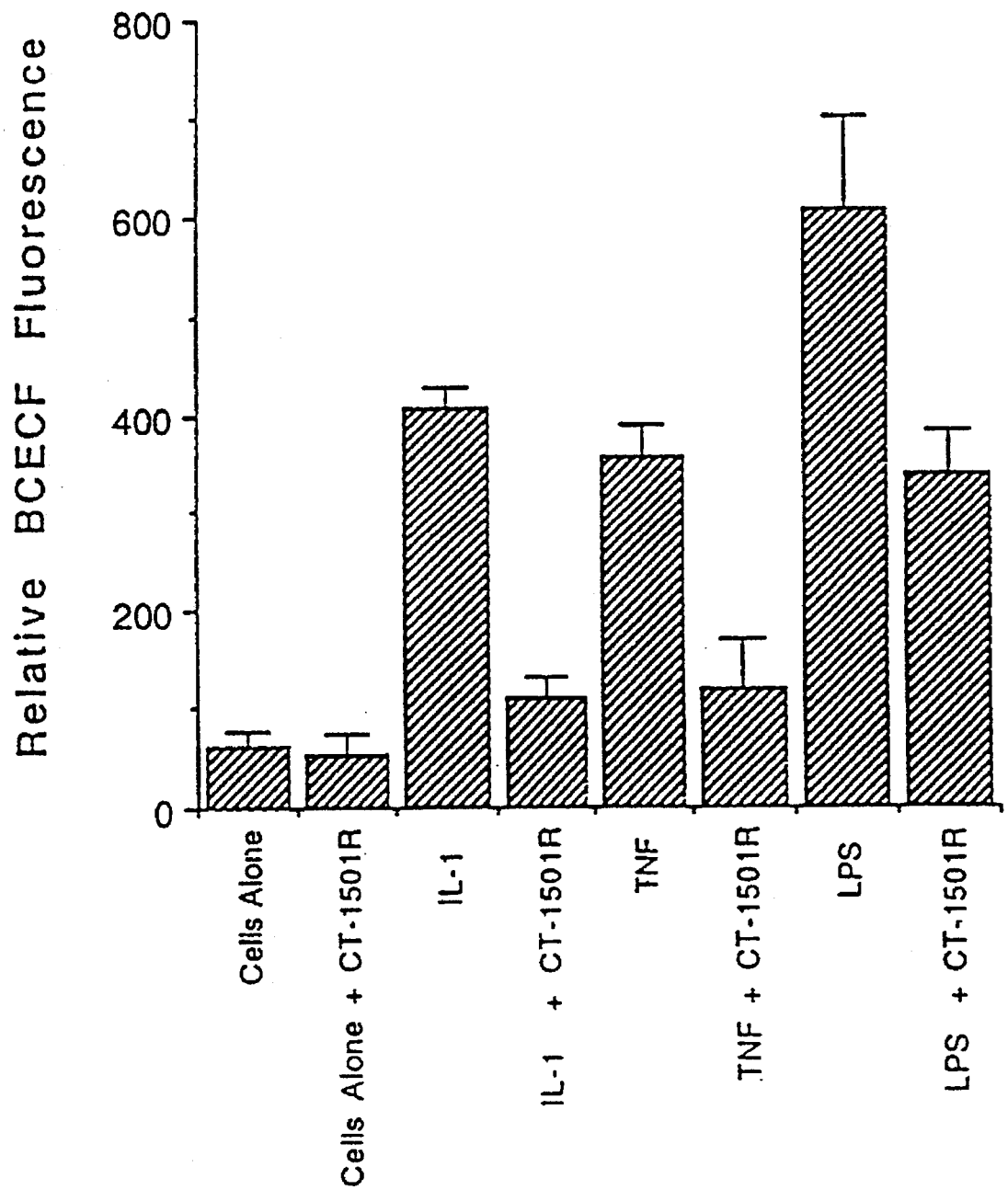
FIG. 21 shows inhibition of adhesion of U937 cells to activated HUVEC. HUVEC were stimulated with either IL-1-α (100 ng/ml); TNF-α (10 ng/ml) or LPS (10 mg/ml) with or without the addition of 250 µM CT1501R one hour prior to addition of the stimulus. Twelve hours later, the cells were assayed for adhesion of BCECF-labeled U937 cells.

Cells of the immune lineage leave the blood by recognizing and binding to vascular endothelial cells. Thereafter immune cells migrate between endothelial cells and surrounding tissue. Models of immune cell adhesion to endothelial cells and extravasation provide predictive models for in vivo manipulation an inflammatory and an atherogenic response. Activation of endothelial cells with TNF-α, IL-1α or LPS up-regulates certain adhesion molecules and increases their adhesiveness for lymphocytes, monocytes, eosinophils and neutrophils. The cell line U937 was used to test the effects of CT1501R on inhibition of adhesion to activated HUVEC. U937 cells express many of the phenotypic characteristics of monocytes including expression of the integrin VLA-4, which mediates monocyte attachment to endothelial cells via vascular adhesion molecule 1 (VCAM), a member of the immunoglobulin superfamily which is expressed on endothelial cells. HUVEC were treated overnight with an activating agent selected from IL-1α, TNF-α or LPS with or without the addition of 250 μM CT1501R, added 1 hour prior to addition of the activating agent. As shown in FIG. 21, there was no significant effect on background attachment of U937 cells to HUVEC by the addition of CT1501R. However, there was a marked suppression in the relative adhesiveness of the activated HUVEC pretreated with CT1501R. This inhibition by CT1501R was observed with stimulation of the HUVEC with either TNF-α, IL-1-α or LPS.

Figure 22:
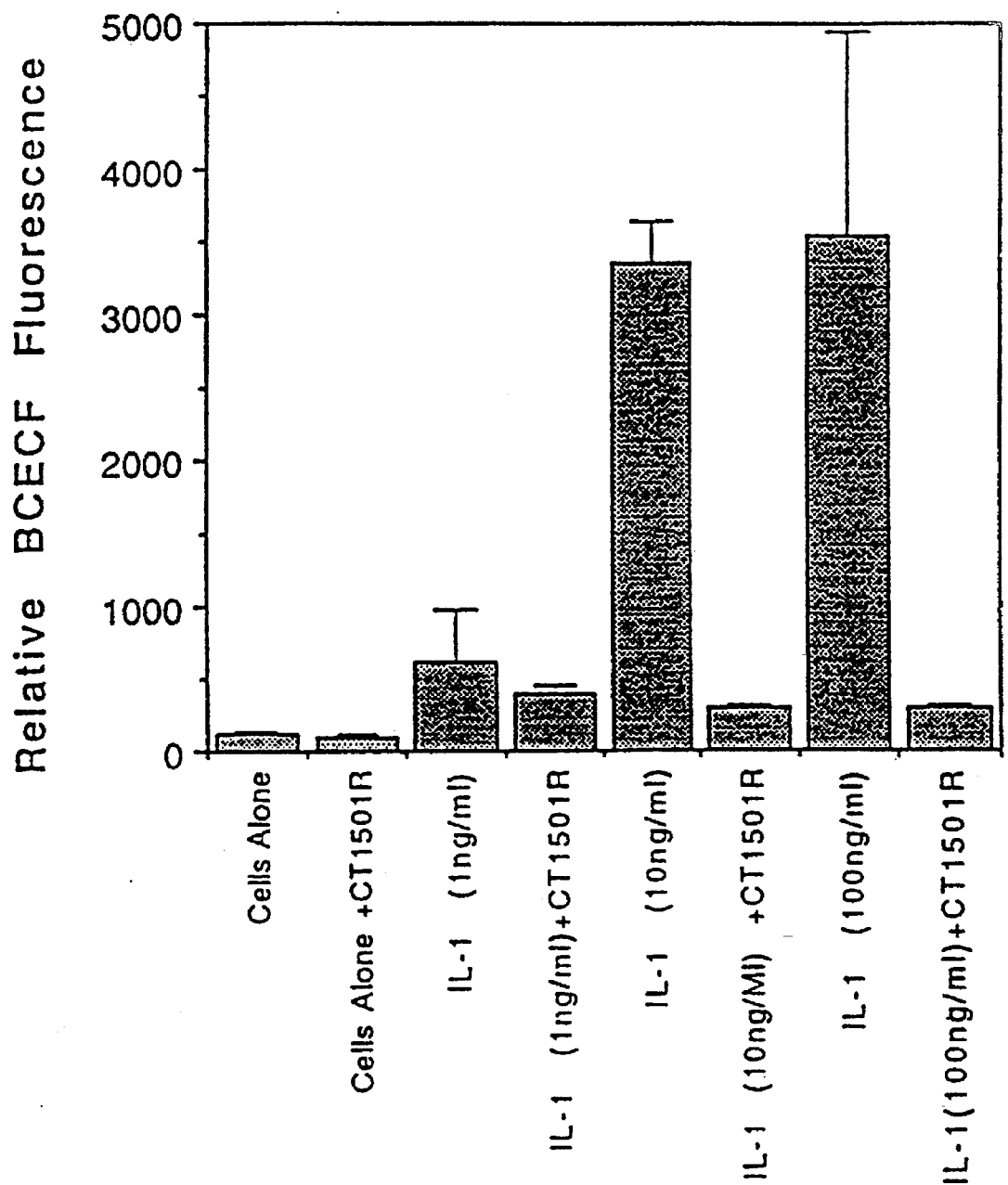
FIG. 22 shows inhibition of adhesion of activated U937 cells to HUVEC. U937 cells were stimulated with various concentrations of IL-1-α with or without the addition of 250 µM CT1501R one hour prior to addition of IL-1-α. Twelve hours later, the U937 cells were stained with BCECF and allowed to adhere to HUVEC.

Conversely, activating U937 cells with IL-1-α also increased their relative adhesiveness to non-stimulated HUVEC (FIG. 22). Pre-treatment of U937 cells with 250 μM CT1501R effectively blocked the IL-1α mediated increase in adhesion to HUVEC to near background levels.

CT1501R inhibited LPS, TNF-α and IL-1α-mediated inflammatory signaling pathways and concomitant cellular responses in peritoneal macrophages, the human U937 histiocytic leukemia cell line, and in human umbilical vein endothelial cells. CT1501R significantly decreased release of the pro-inflammatory cytokines TNF-α and IL-1α from peritoneal macrophages stimulated with LPS. The IC50 for TNF-α inhibition using 10 μg/ml LPS stimulation was approximately 30 μM. CT1501R blocked TNF-α release from IL-1α activated PEC. CT1501R inhibited the increase in adhesion of U937 cells to TNF-α, IL-1α or LPS activated HUVEC. Finally, CT1501R inhibited IL-1α-induced activation and increased adhesiveness of U937 cells to non-stimulated HUVEC.

EXAMPLE 8

This example illustrates nude mouse hair studies involving topical application of CT1501R. Six to eight week old, female, nu/nu mice from Charles River Laboratories were housed at Biosupport Research Support Services (Seattle, Wash.) in autoclaved micro isolator units with hyperchlorinated autoclaved water, irradiated rodent chow and kept under a laminar flow hood. Caging was changed weekly, and water was changed twice weekly. The mice were acclimated for 5 days before beginning each study.

The first topical formulation was prepared by adding CT1501R to a heated hydrophilic ointment (USP) at a 1% concentration, and allowed to solidify.

Nude mice were painted twice daily for 16 days with the first topical formulation of CT1501R on the left flank and another compound in the same base on the right flank with sterile applicators. Mice were handled under the laminar flow hood with applicator wearing face mask and sterile gloves. After 16 days, one mouse was sacrificed by cervical dislocation and skin biopsies were taken of the treated areas of the shoulder/flank and from the non-treated area of the dorsal pelvis (rump). Specimens were placed in 10% buffered formalin solution. Biopsies were sent to a veterinary dermopathologist for histopathology. Six weeks following treatment, a second mouse was euthanatized and biopsied the same as the first. Samples were sent for histopathology.

The results from the first experiment show that treated sections had significantly more normal appearing hair follicles than the non treated sections. Numerous hair shafts were seen exiting the follicles in the treated sections vs. none in the non treated sections for both CT1501R and the other compound.

In a second experiment, topical application of CT1501R was performed along with a commercial topical minoxidil preparation (Rogaine®, Upjohn) that is approved for a hair growth indication. Five to six week old, female, nu/nu mice from Bantin and Kingman Universal were housed at Biosupport Research Support Services (Seattle, Wash.) in autoclaved micro isolator units with hyper chlorinated autoclaved water, irradiated rodent chow and kept under a laminar flow hood. Caging was changed weekly, and water was changed twice weekly. Mice were acclimated for 7 days before beginning study.

CT1501R, and two other compounds were prepared in a topical formulation of 60% ETOH, 10% water and 30% PEG along with vehicle only. Minoxidil was purchased at the commercial preparation Rogaine® from a local pharmacy. Rogaine® is sold in the same formulation base. Mice were identified by unique tail markings specific for each test article. Two mice per group were treated with CT1501R and another compound. One mouse was treated with each of vehicle and minoxidil. The mice were handled under the laminar flow hood with the applicator wearing face mask and sterile gloves. Each mouse was treated twice daily with a separate sterile applicator to avoid contamination of the solutions or the mice. All mice were applied a strip of appropriate test article along the center line of the back from the base of the skull to the base of the tail, approximately 1.5 cm wide. After 34 days all mice were euthanatized by overdose of halothane anesthesia. Skin biopsies were taken from each of the 7 mice over the nape of the neck between the scapulas (approximate size was 1×1.5 cm). All specimens were blotted on gauze to remove blood and fluids, affixed to a cut piece of wooden tongue depressor, and placed specimen side down in separately marked containers with 10% buffered formalin. Specimens were shipped to a veterinary dermatopathologist for qualitative histopathological determinations.

Subjective examination revealed that the vehicle treated mouse (control) had the least well developed hair follicles. A fair response to treatment was evident in the minoxidil treated mouse. CT1501R and the other compound treated mice had the greatest concentration of hair folicles. Further, visual inspection of the mice revealed that the CT1501R mice were the most "hairy" of a group consisting of CT1501R, minoxidil and control. Therefore, CT1501R is at least as good at promoting hair growth in this model as minoxidil. Accordingly, a topical formulation of 1–4% CT15001R (by weight) is an effective therapeutic composition for treating baldness and promoting hair growth.

EXAMPLE 9

This example illustrates the effect of CT1501R on survival in mice given a lethal dose of endotoxin. We determined if CT1501R protects against endotoxin induced lethality in a murine model. Septic shock was modeled by endotoxin injection of 6–8 week old female Balb/c mice similar to previously published reports (Ashkenazi et al. *Proc. Natl. Acad. Sci. U.S.A.* 88: 10535–10539, 1991.) under protocols approved by the Animal Use Committee of the Biomembrane Institute, Seattle, Wash. Animals were injected intravaneously (i.v.) with an approximate $LD_{100}$ dose (10 µg/g) of *Salmonella abortus* equi-derived endotoxin (Sigma Chemical Co., L-1887) in phosphate buffered saline (PBS). CT1501R at a dose of 100 µg/kg was injected intraperitoneally (IP) 3 times per day (100 ml/injection). Control mice were injected at the same times with a similar volume of vehicle control (PBS). Survival was followed for at least 72 hours.

For ELISA measurements of cytokine levels in plasma, blood was collected by retro-orbital or cardiac puncture of anesthetized mice, immediately centrifuged and the EDTA plasma stored at –70° C. Particulate free plasma was thawed on ice and cytokine levels determined utilizing commercial ELISA assays with normal mouse plasma used to generate standard cubes. Murine tumor necrosis factor-α and interleukin-α kits were purchased from Genzyme (Cambridge, Mass.) and Endogen (Boston, Mass.), respectively. Each data point was an average of two ELISA measurements made from EDTA serum pooled from three mice. The data summarized in Table 3 were compiled from two independent experiments; data from Table 4 and 5 were from single experiments of three mice per data point.

Figure 5:
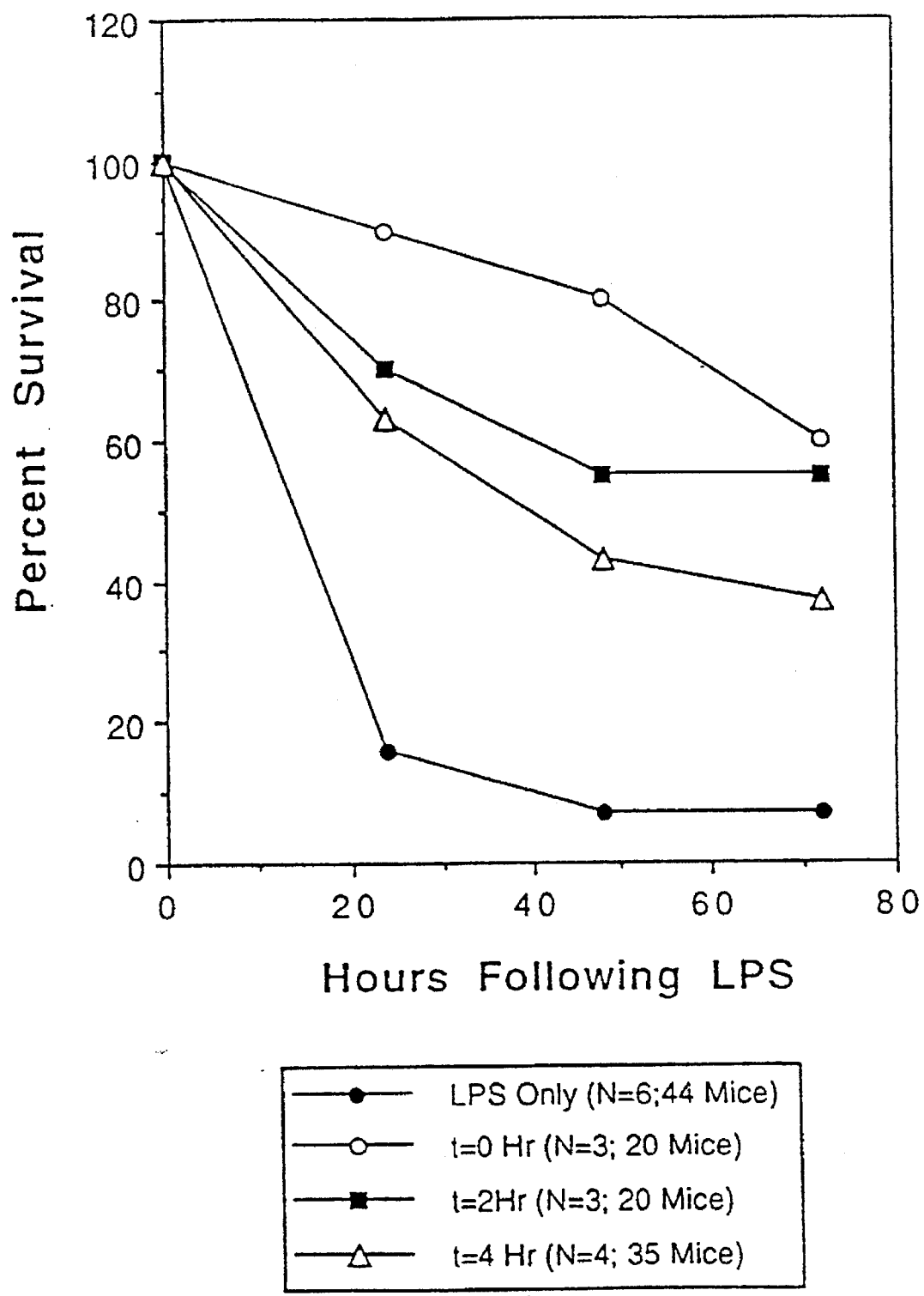
FIG. 5 shows inhibition of endotoxin induced lethality in mice by CT1501R as a cumulative percent survival of mice from up to 6 independent experiments (N=the number of experiments). Animals were treated with 10 μg/gm of LPS (i.v.) Immediately following the LPS (t=0), 2 hrs after the LPS (t=2) or 4 hrs following LPS (t=4) the mice were treated with their first treatment of CT1501R (100 mg/kg, i.p.). The mice were treated with CT1501R three times per day thereafter, and animal survival was monitored.

Ten mice were treated each with PBS alone or CT1501R alone on the same schedule as the experimental mice. There were no adverse effects noted and survival was 100% throughout the course of the experiment (data not shown). Endotoxin survival data were summarized from a total of six (6) independent experiments. Summary Table 1 details the results of each of the six experiments. Cumulative percent survival is given in Table 2 and plotted as FIG. 5. In FIG. 5, each time point represents a minimum of three (3) experiments comprising at least twenty (20) mice per group. A probability analysis of the survival data using a Fisher's Exact One Tailed Test is given as Table 3. Significant protection was conferred if CT1501R was administered immediately after the LPS treatment. The cumulative percent survival at 72 hours post LPS treatment was 60% compared to 7% for the LPS-only treated animals (p=<0.0005; Table 3).

The effect of delaying the time of administration of CT1501R following the LPS treatment is also shown in FIG. 5. Animals were treated with LPS and given CT1501R either two or four hours after the LPS treatment. Again, CT1501R conferred significant protection. Survival of the CT1501R treated mice was 55% at 2 hrs and 37% at 4 hrs compared to 7% for the LPS-only treated mice (p=0.0005 and p=0.001; respectively; Table 3).

Figure 6:
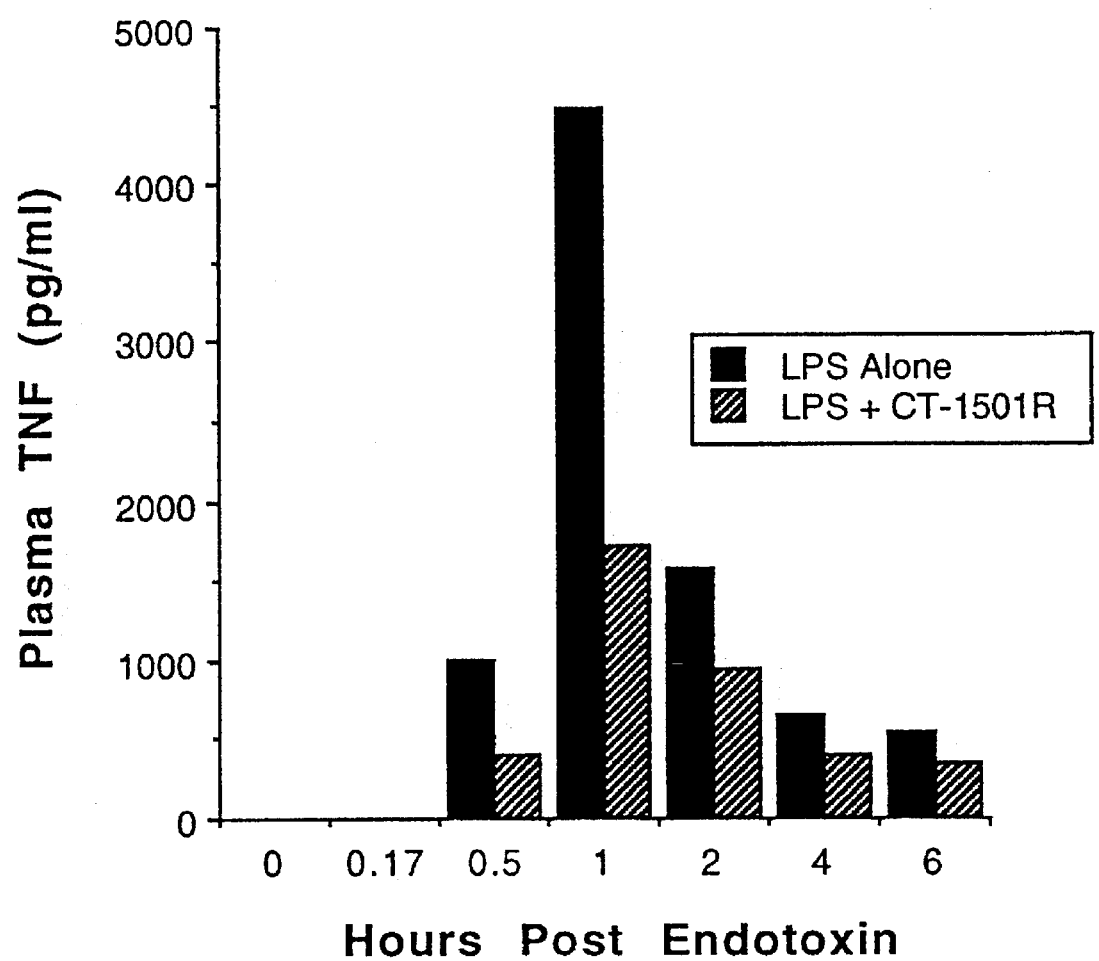
FIG. 6 shows mouse serum TNF-$\alpha$ levels following endotoxin treatment. Each point represents the average of two experiments compiled from the average of duplicate ELISA measurements with each experimental point representing pooled plasma from three mice.

Levels of TNF-α, IL-1α and IL-6 were measured in the plasma of mice as a function of time following treatment with *S. abortus* endotoxin. These data were compared to animals treated with endotoxin followed immediately with a single i.p. injection of CT1501R. TNF-α levels peaked within 1 hour of treatment of endotoxin (Table 4 and FIG. 6). Treatment of the mice with CT1501R decreased the levels of TNF-α in the EDTA plasma of endotoxin treated mice at all time points measured. In particular, peak levels of TNF-α at 0.5 and 1 hour post endotoxin were decreased 2.5 and 2.6 fold respectively in the CT1501R treated mice.

Figure 7:
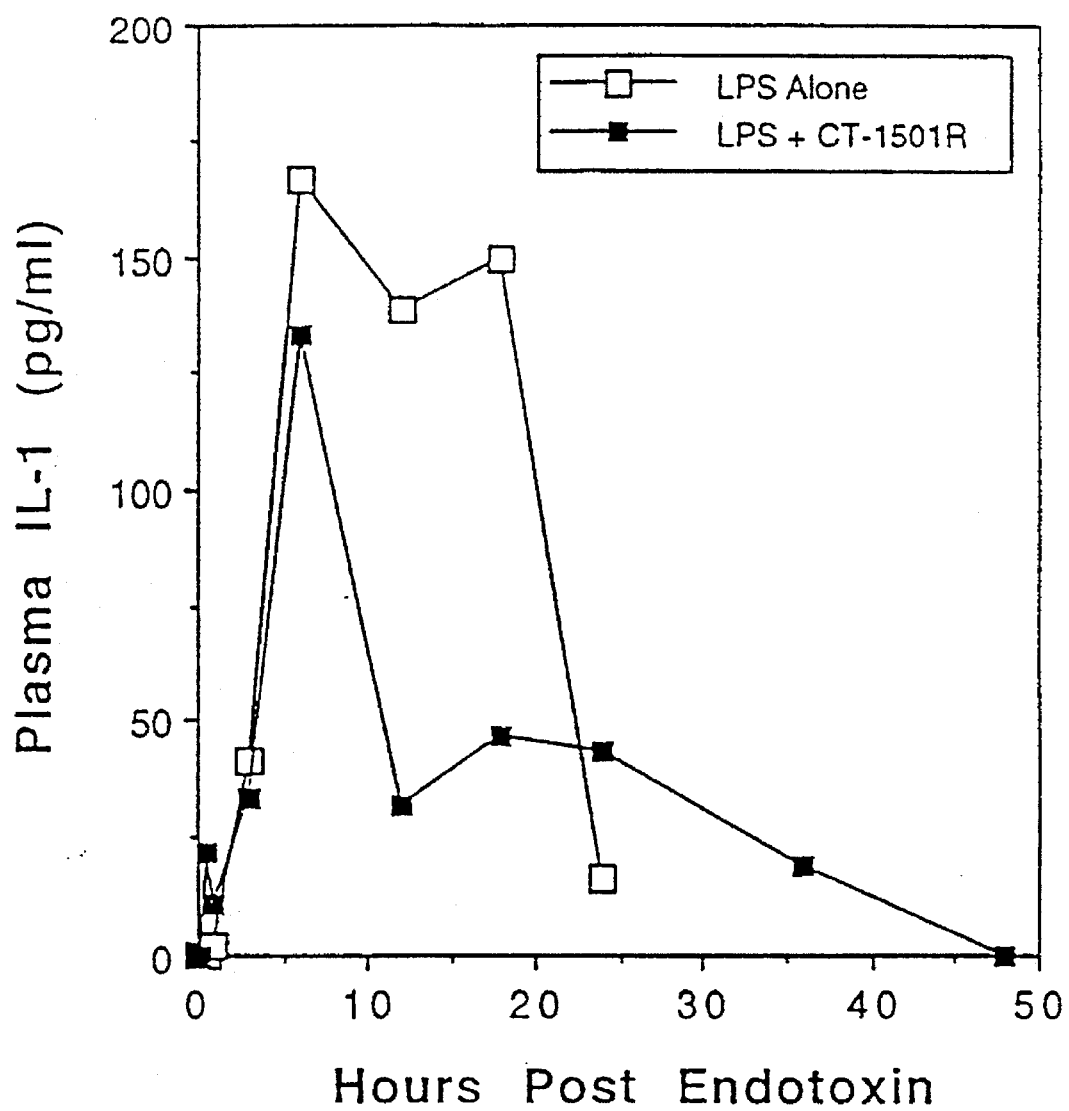
FIG. 7 illustrates data from mouse plasma IL-1$\alpha$ ELISA measurements. Data were compiled from an average of duplicate ELISA measurements from a single experiment with each point representing pooled serum from three mice.
Figure 8:
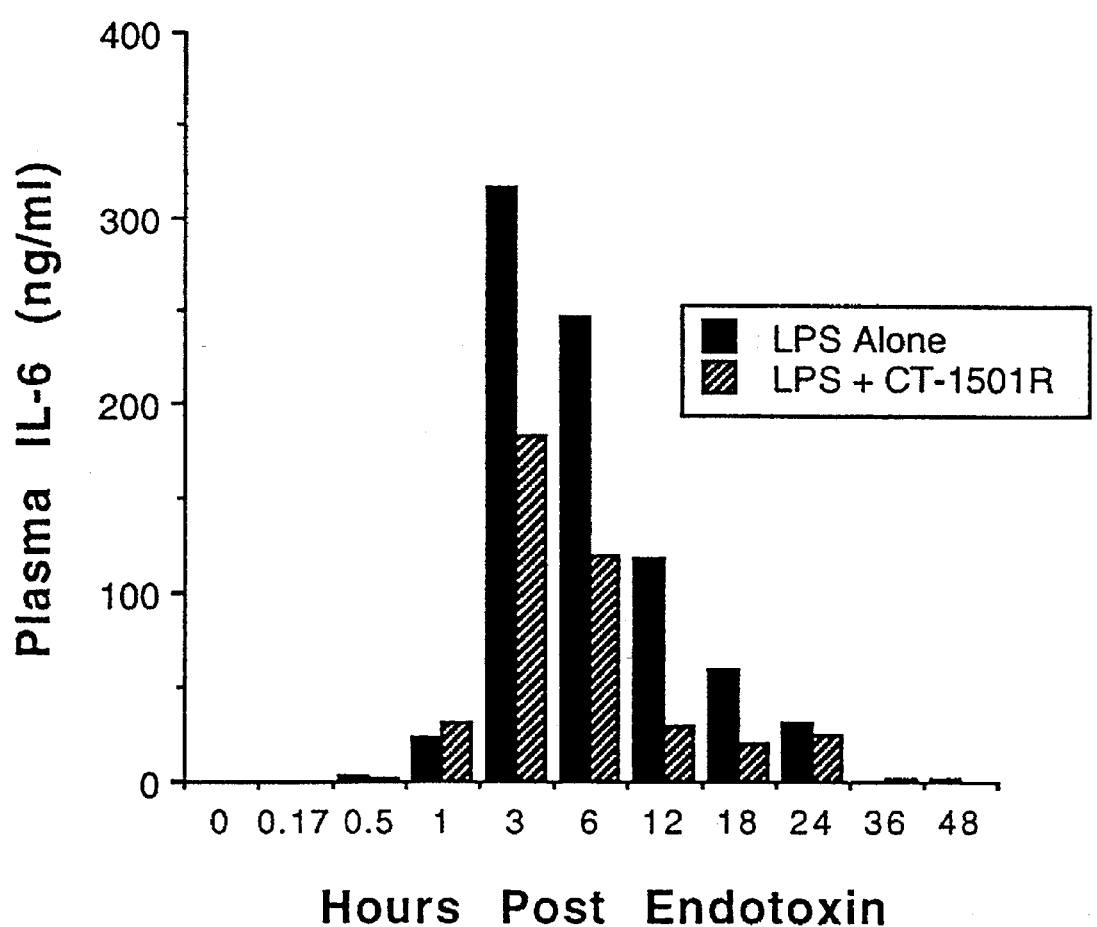
FIG. 8 illustrates data from mouse plasma IL-6 ELISA measurements. Data are compiled from the average of duplicate ELISA measurements from a single experiment with each point representing pooled plasma from three mice.

Plasma levels of IL-1α were also decreased by treatment with CT1501R immediately following the endotoxin (Table 5; FIG. 7). In particular, peak levels observed at 6, 12 and 18 hours post endotoxin were decreased 1.2, 4.3 and 3.2-fold, respectively. Finally, IL-6 measurements were made in a similar manner (Table 6, FIG. 8). Peak plasma levels at 3, 6 and 12 hours were also decreased in the CT1501R treated animals (1.7, 2.0 and 4.1-fold decrease, respectively).

CT1501R significantly enhanced survival in mice that received a dose of endotoxin that was lethal to 41 of 44 mice. Survival was improved compared to control when CT1501R was administered simultaneous with endotoxin or after 2 or 4 hours following endotoxin treatment. Administration of a single dose of CT1501R immediately following the endotoxin significantly decreased peak plasma levels of TNF-α, IL-1α and IL-6.

TABLE 1

Survival data from six independent mouse sepsis experiments.

| Expt. # | Time of CT-1501R Post LPS | Hours Post LPS (Number Surviving/Total) | | |
|---|---|---|---|---|
| | | 24 Hr | 48 Hr | 72 Hr |
| 1 | LPS only | 2/4 | 0/4 | 0/4 |
| | t = 0 Hr | 4/5 | 4/5 | 4/5 |
| | t = 2 Hr | 4/5 | 3/5 | 3/5 |
| 2 | LPS only | 0/5 | 0/5 | 0/5 |
| | t = 0 Hr | 5/5 | 5/5 | 5/5 |
| | t = 2 Hr | 5/5 | 5/5 | 5/5 |

TABLE 1-continued

Survival data from six independent mouse sepsis experiments.

| Expt. # | Time of CT-1501R Post LPS | Hours Post LPS (Number Surviving/Total) | | |
|---|---|---|---|---|
| | | 24 Hr | 48 Hr | 72 Hr |
| 3 | LPS only | 1/5 | 1/5 | 1/5 |
| | t = 4 Hr | 5/5 | 3/5 | 3/5 |
| 4 | LPS only | 1/10 | 1/10 | 1/10 |
| | t = 4 Hr | 7/10 | 5/10 | 5/10 |
| 5 | LPS only | 0/10 | 0/10 | 0/10 |
| | t = 0 Hr | 9/10 | 7/10 | 3/10 |
| | t = 2 Hr | 5/10 | 3/10 | 3/10 |
| | t = 4 Hr | 7/10 | 4/10 | 2/10 |
| 6 | LPS only | 3/10 | 1/10 | 1/10 |
| | t = 4 Hr | 3/10 | 3/10 | 3/10 |

TABLE 2

Cumulative mouse survival from data derived from Table 1.

| No. Expts. | Time of CT-1501R Post LPS | Hours Post LPS (Number Surviving/Total) | | |
|---|---|---|---|---|
| | | 24 Hr | 48 Hr | 72 Hr |
| n = 6 | LPS only | 7/44 | 3/44 | 3/44 |
| n = 3 | t = 0 Hr | 18/20 | 16/20 | 12/20 |
| n = 3 | t = 2 Hr | 14/20 | 11/20 | 11/20 |
| n = 4 | t = 4 Hr | 22/35 | 15/35 | 13/35 |

TABLE 3

Fisher's Exact P Values (one tailed) for the mouse sepsis survival data in Table 2.

| No. Expts. | Time of CT-1501R | P Value (Hours Post LPS) | | |
|---|---|---|---|---|
| | | 24 Hr | 48 Hr | 72 Hr |
| n = 6 | LPS Only | | | |
| n = 3 | t = 0 Hr | <0.0005 | <0.0005 | <0.0005 |
| n = 3 | t = 2 Hr | <0.0005 | 0.0005 | 0.0005 |
| n = 4 | t = 4 Hr | <0.0005 | 0.0002 | 0.001 |

TABLE 4

Averaged Data From Mouse Plasma TNF-α ELISA Measurements

| Hours Post LPS | Plasma TNF (pg/ml) | |
|---|---|---|
| | LPS Only | LPS + CT-1501R |
| 0 | 0 | 0 |
| 0.17 | 8 | 6 |
| 0.5 | 990 | 390 |
| 1 | 4480 | 1728 |
| 2 | 1585 | 940 |
| 4 | 655 | 400 |
| 6 | 545 | 350 |

TABLE 5

Data From Mouse Plasma IL-1α ELISA Measurements

| Hours Post LPS | Plasma IL-1 (pg/ml) | |
|---|---|---|
| | LPS Only | LPS + CT-1501R |
| 0 | 0 | 0 |
| 0.17 | 0 | 0 |
| 0.5 | 0.01 | 22 |
| 1 | 2.25 | 10.8 |
| 3 | 41.3 | 33.2 |
| 6 | 166 | 133 |
| 12 | 139 | 32.3 |
| 18 | 150 | 46.7 |
| 24 | 16.6 | 43.5 |
| 36 | all dead | 18.8 |
| 48 | all dead | 0 |

TABLE 6

Data From Mouse Plasma IL-6 ELISA Measurements.

| Hours Post LPS | Plasma IL-6 (ng/ml) | |
|---|---|---|
| | LPS Only | LPS + CT-1501R |
| 0 | 0 | 0 |
| 0.17 | 0.2 | 0.14 |
| 0.5 | 3.86 | 1 |
| 1 | 24 | 31.8 |
| 3 | 317 | 183 |
| 6 | 247 | 121 |
| 12 | 119 | 29.6 |
| 18 | 59 | 19.8 |
| 24 | 31 | 25.6 |
| 36 | 0 | 1.64 |
| 48 | 2 | 0.4 |

EXAMPLE 10

This example illustrates the effect of CT1501R on 5-fluorouracil (5-FU) induced bone marrow suppression in mice. We determined if CT1501R influenced the time required for hematopoietic reconstitution following cytotoxic chemotherapy in a murine model. Female Balb/C mice (VAF, Charles River Laboratories, 6–8 wks of age approximately 17.3–18.5 g) were treated with 5-FU at a dose of 200 mg/kg intraperitoneally (i.p.).in experiment 1 or 190 µg/kg in experiment 2. CT1501R or vehicle control was given at a dose of 100 µg/kg i.p. bid starting 1 day prior to 5-FU and was continued until the last mice were sacrificed on day 13 in experiment 1 and day 15 in experiment 2. Controls included mice treated with CT1501R or vehicle without 5-FU. Mice (4 per group) were sacrificed starting 2 days after 5-FU by cardiac puncture under halothane anesthesia followed by cervical dislocation and had total white blood cell counts and differential counts performed. Platelet counts were performed using phase-contrast microscopy in duplicate. Femurs were harvested and the number of granulocyte-macrophage colony forming cells (CFU-GM) per femur were measured using a standard assay (Terry Fox Laboratories, Vancouver, British Columbia) using pokeweed mitogen spleen conditioned medium as the growth factor. Each femur was plated separately in triplicate and the mean and means for each experimental point was calculated. Standard deviations used for statistical analysis were deviations of the mean number of colonies measured for each femur.

The mice treated with vehicle control or CT1501R had no apparent adverse effects. The mice treated with the vehicle control alone had a rise in absolute neutrophil count (ANC) and white blood cell counts (WBC) with time which was not seen in the CT1501R treated mice. These differences were significantly different from day 0 values on days 4 and 8 (p=0.012 and p=0.016, respectively; two-tailed student T test). When compared to mice receiving CT1501R, the control treated mice had significantly higher white blood cell counts on day 4 (p=0.009) and significantly higher neutrophil counts on day 12 (p=0.028). Control treated mice had a significant rise in granulocyte count on day 12 compared to the value on day 0 (p=0.028). The CT1501R treated mice's WBC and ANC remained within 1 SD of control values.

Figure 10:
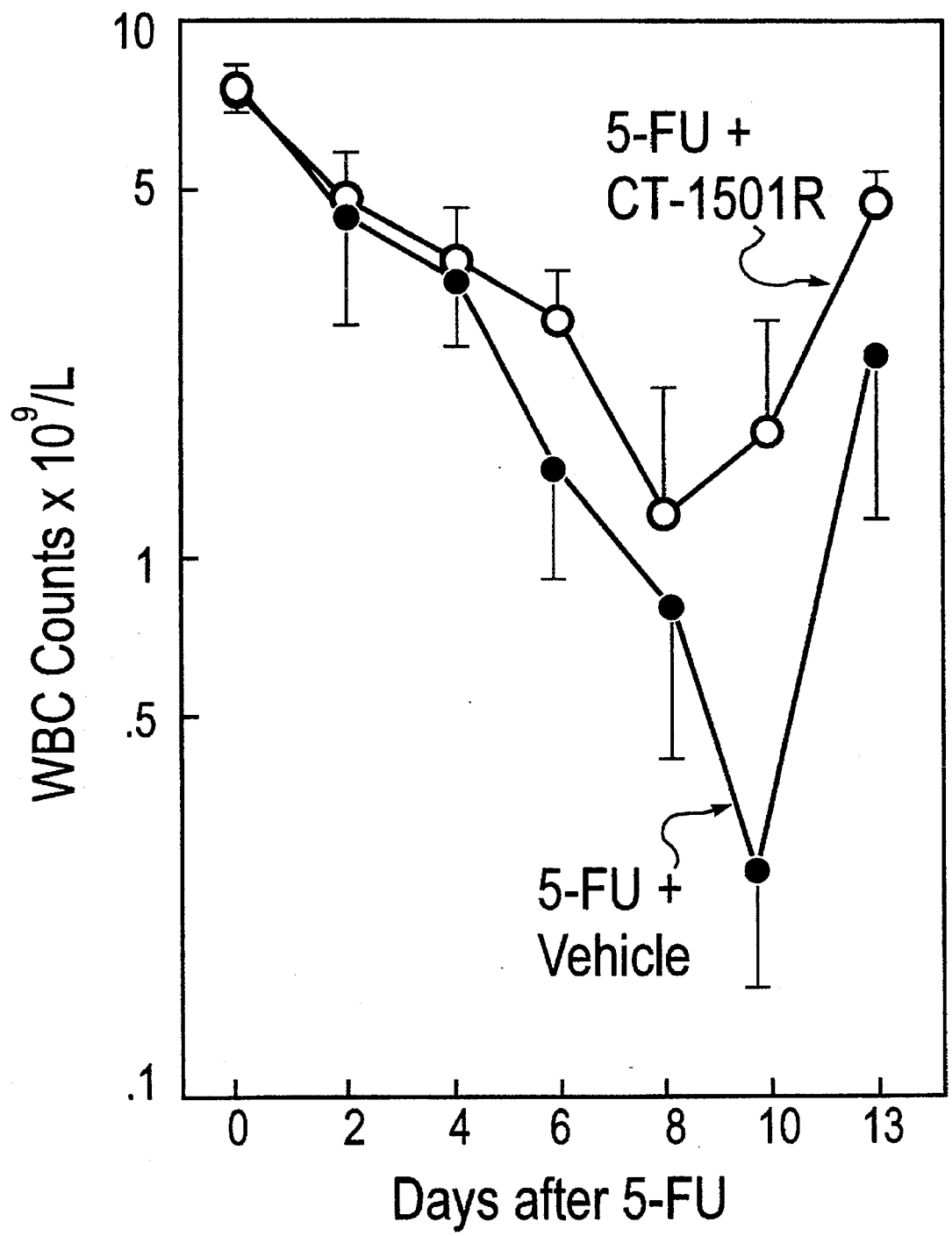
FIG. 10 shows the mean WBC of mice treated with 5-fluorouracil on day 0 and CT1501R or vehicle control twice daily starting on day -1. This experiment, reported in FIGS. 10–13, is an in vivo model for hematopoiesis. Groups of 4 mice were phlebotomized at each time point. The values on the graph represent the means±1 SD.

The WBC's of 5-FU treated mice were significantly lower in vehicle treated controls than in CT1501R treated mice on days 6 and 10 (p=0.019 and 0.036, respectively) (FIG. 10). On differential blood counts all cells had the morphology of lymphocytes in both groups on days 6, and 8. Some monocytes and rare granulocytes were noted in the CT1501R treated animals on day 10. On day 13, CT1501R had a mean±SD ANC of 440±17/mm$^3$ while the control mice had 180±10/mm$^3$ (P=0.05) (FIG. 10).

Figure 13:
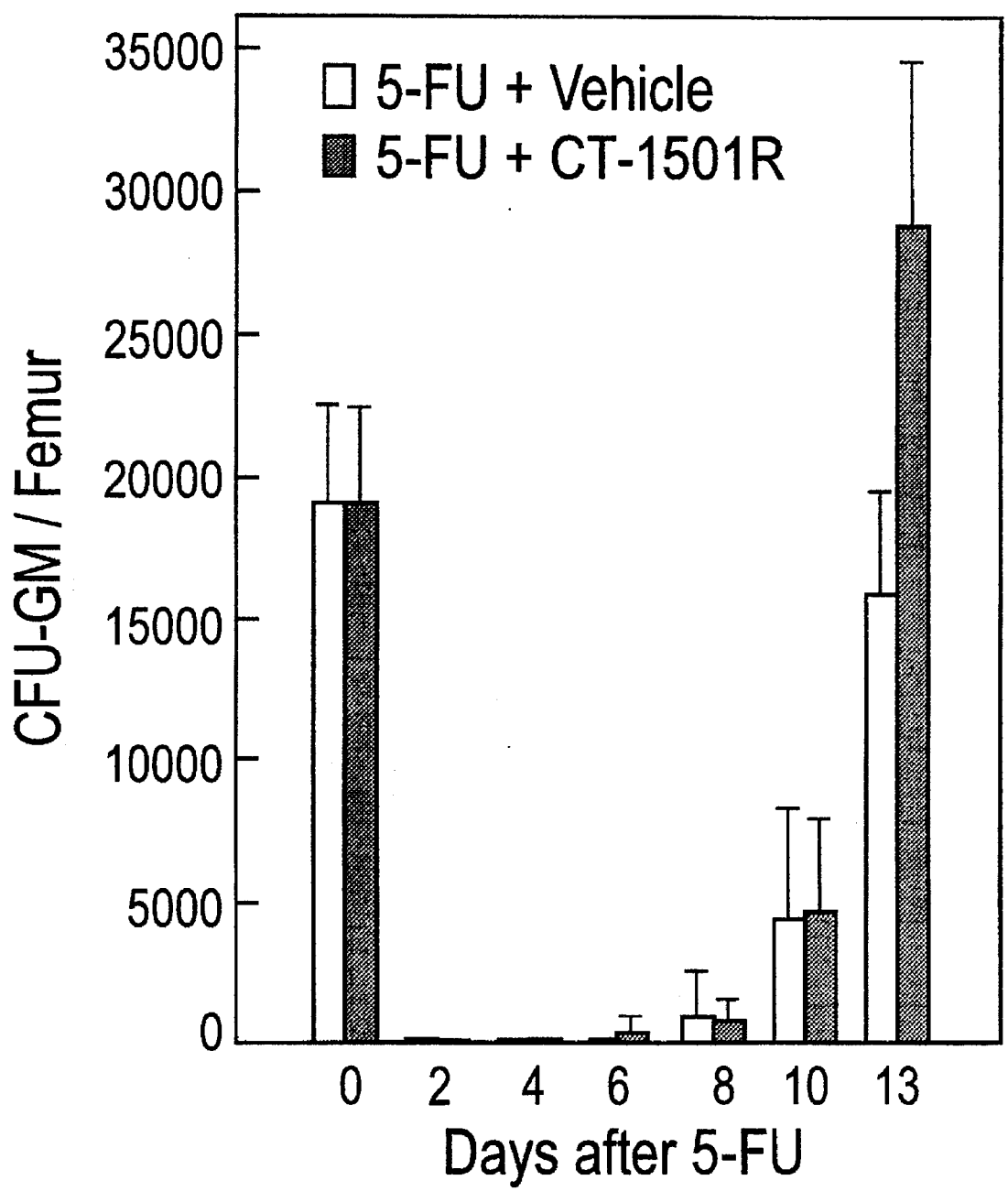
FIG. 13 shows the mean CFU-GM/femur of mice treated with 5-fluorouracil on day 0 and CT1501R or vehicle control twice daily starting on day 0. Groups of 4 mice were sacrificed and had one femur harvested at each time point. The values on the graph represent the means±1 SD of the mean number of colonies per each individual tested in triplicate cultures.
Figure 14:
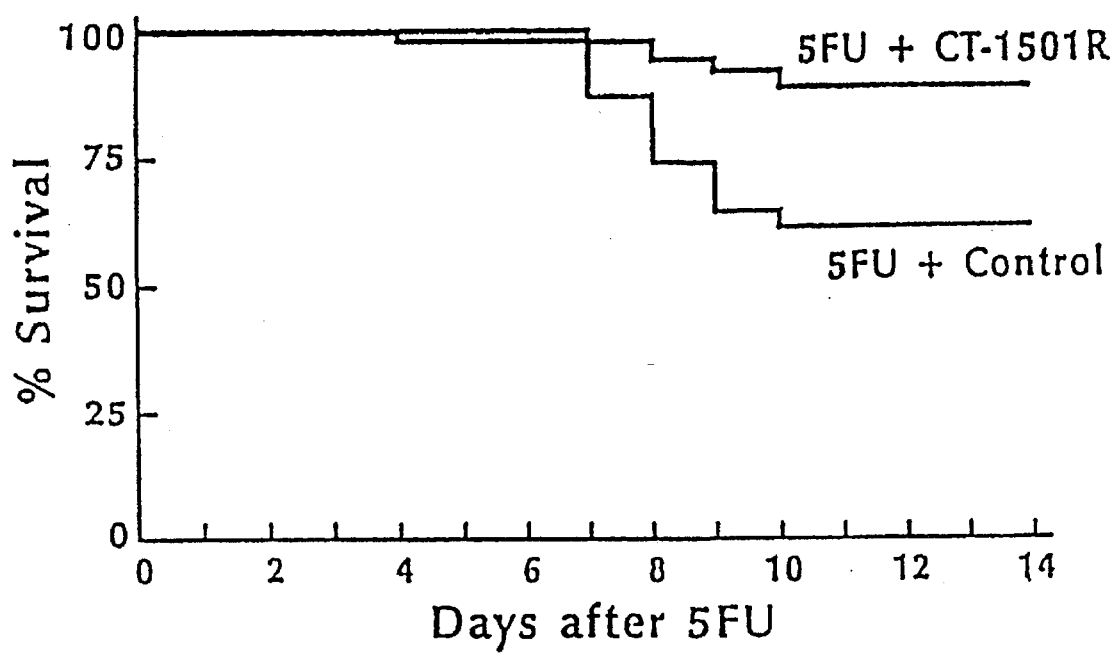
FIG. 14 shows the mouse survival data in the experiment described in FIG. 13 in the form of a Kaplan-Meier plot showing improved survival with CT-1501R.
Figure 15:
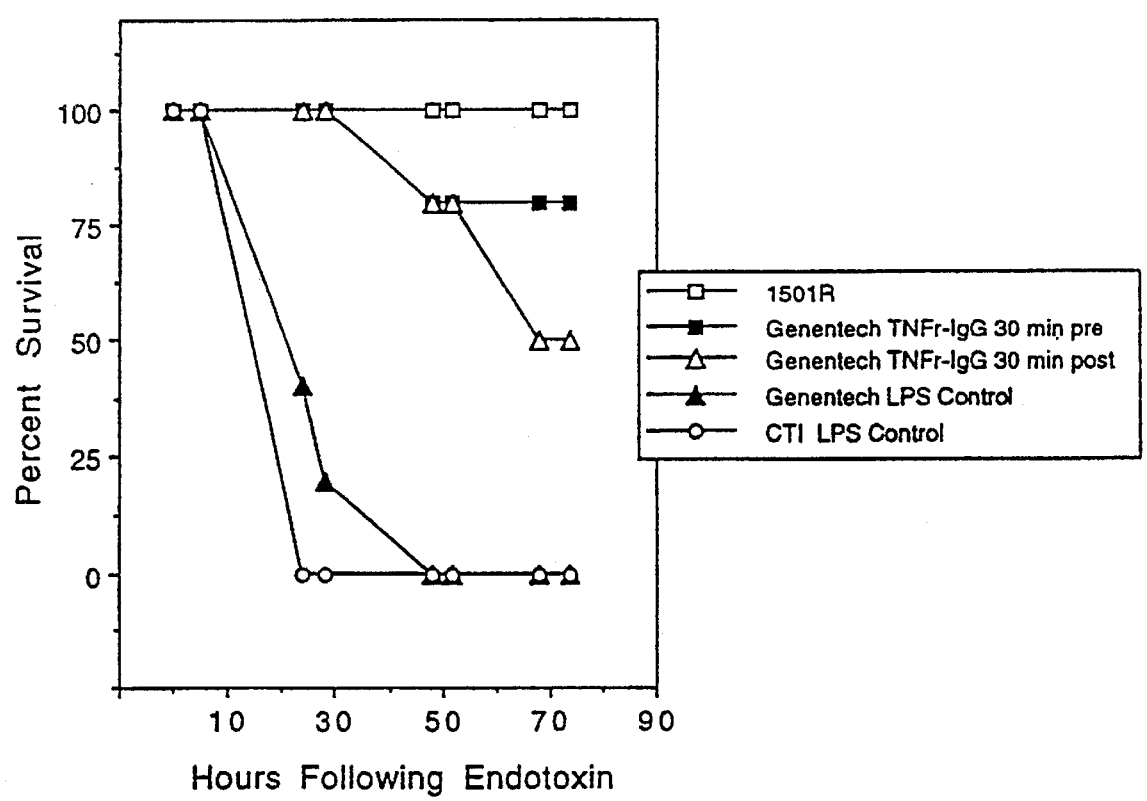
FIGS. 15 and 16 show a comparison of CT1501R with published results from another septic shock drug, the bifunctional TNF receptor made by Genentech (Ashkenazi et at., *Proc. Natl. Acad. Sci. USA* 88:10535, 1991). Both drugs were administered approximately simultaneously (FIG. 15) or two hours following (FIG. 16) a lethal LPS (endotoxin) administration,. In this series of comparative in vivo experiments, CT1501R consistently was better at improving survival than Genentech's TNF receptor irrespective of the time of drug administration.
Figure 16:
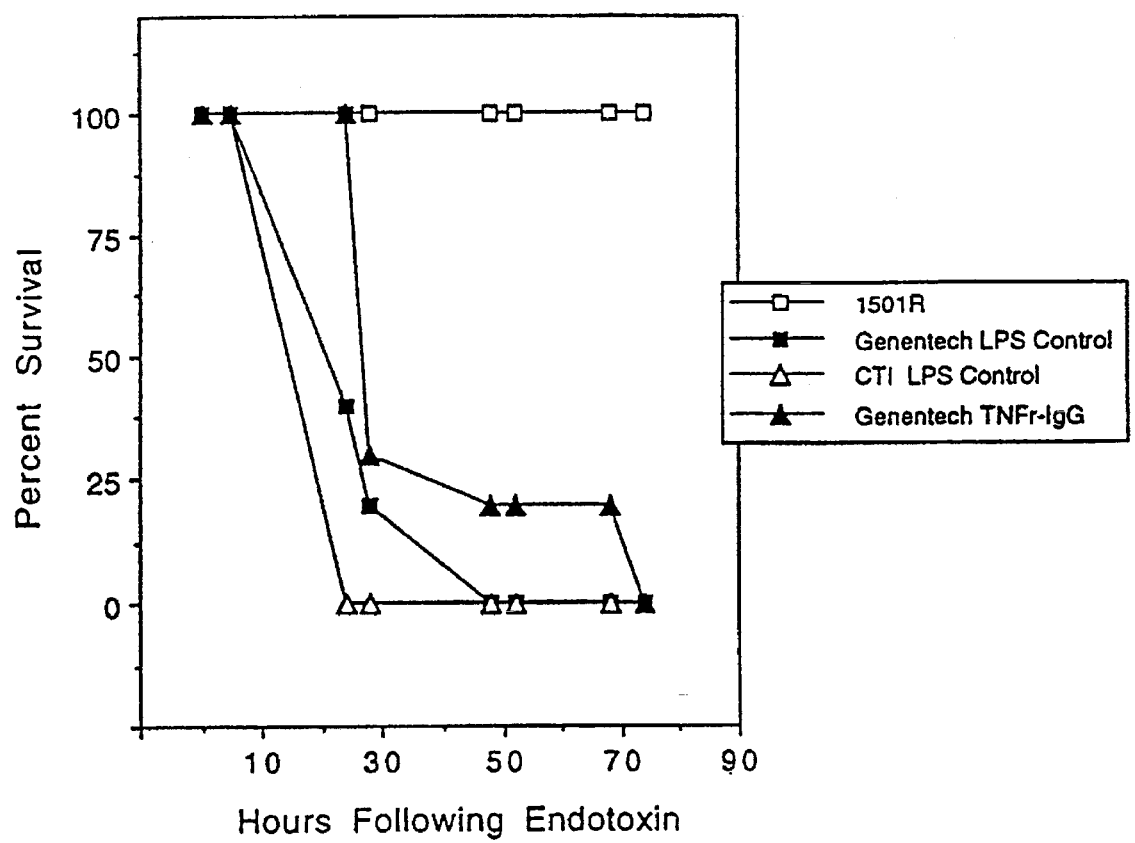
Figure 17:
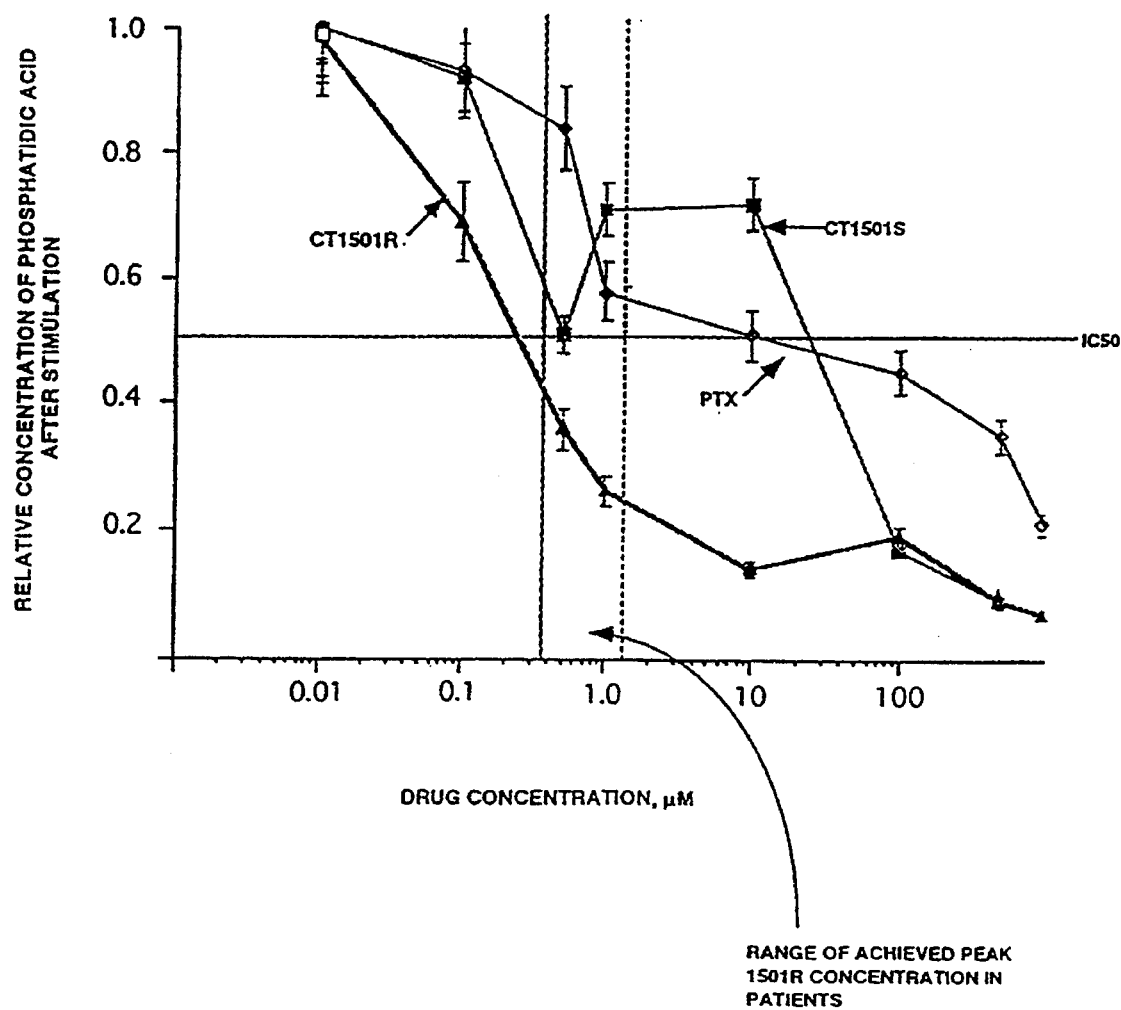
FIG. 17 illustrates a comparison of CT1501R, its S isomer CT1501S, and PTX on in vitro inhibition of lysophosphatidic acid acyl transferase (LPAAT), an enzyme involved in second messenger signaling. As can be seen, only CT1501R significantly inhibited enzyme activity at IC50 concentrations that would be achievable in a clinical setting. LPAAT activity was determined in 3T3 Ras-transformed fibroblasts stimulated with IL-1β.

An estimate of recovery of hematopoietic progenitor cells is provided by measurement of the number of CFU-GM/ femur. Following 5-FU treatment both vehicle control and CT1501R treated mice had suppression of CFU-GM to near unmeasurable levels until day 8 when recovery began (FIG. 13). By day 13, there was significant divergence. CT1501R treated mice had significantly more CFU-GM/femur on day 13 than either the vehicle control animals (p=0.024) and animals sacrificed before any treatment on day 0 (p=0.05) indicating that there was an overshoot of progenitor recovery.

Figure 11:
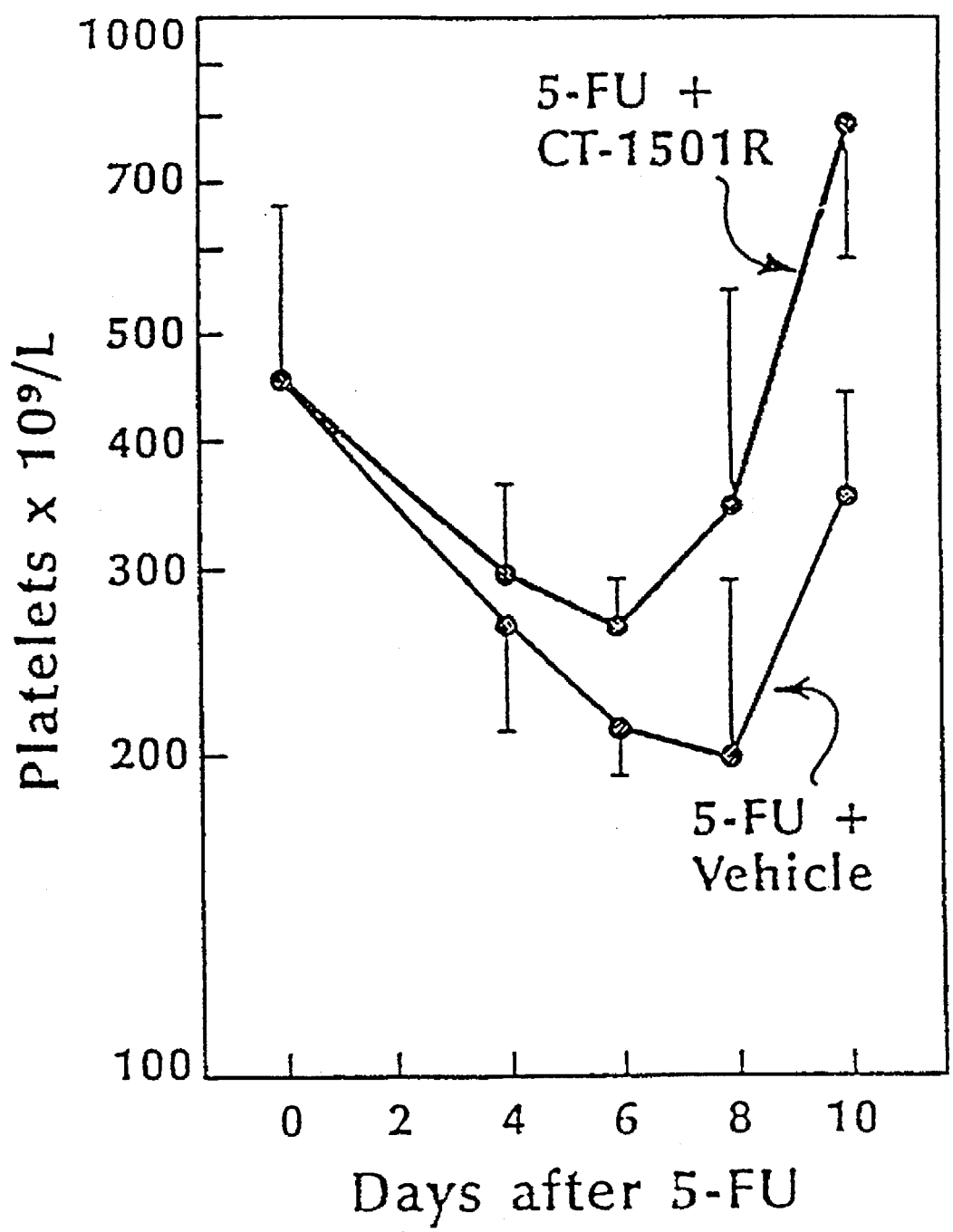
FIG. 11 shows the mean platelet counts of mice treated with 5-fluorouracil on day 0 and CT1501R or vehicle control twice daily starting on day 0. Groups of 4 mice were phlebotomized at each time point. The values on the group represent the means±1 SD.

Experiment 2 was similar to experiment 1 with the following exceptions: (1) the dose of 5-FU was decreased to 185 mg/kg; (2) daily blood draws were performed between days 10 and 15; and (3) platelet counts were performed. Results from experiment 2 are displayed graphically in FIGS. 10–13. As in the first experiment, mice treated with CT1501R had significantly higher WBC's (FIG. 10) Neutrophil recovery was accelerated in the CT1501R treated mice (FIG. 12). The platelet count nadir and rate of recovery were also increased compared to vehicle control animals (FIG. 11) The number of cells per femur was increased during hematopoietic recovery compared to control animals as was the number of CFU-GM/femur (FIG. 13).

In mice that received a highly marrow suppressive dose of 5-FU, CT1501R treatment increased the rate of rise in neutrophil counts and the rate of marrow repopulation with committed myeloid progenitor cells. CT1501R inhibited 5-FU induced suppression of the total WBC at each time point measured. However, until day 10, the increase was in cells with the morphologic appearance of small lymphocytes. On day 13 in experiment 1 and on day 10 in experiment 2, the neutrophils in mice treated with C11501R became significantly higher than in vehicle control treated mice. The stimulation of hematopoietic recovery by CT1501R also affected the megakaryocyte lineage. Test animals had a significantly higher platelet nadir than control animals and had a more rapid rise in platelet count and a greater overshoot than did vehicle controls.

Stimulation of hematopoiesis was also evidenced by both the return in marrow cellularity and the quantification of marrow progenitor cells. CT1501R treated mice had an approximately two-fold increase in the number of CFU-GM/ femur during hematopoietic recovery compared to control animals.

In animals that did not receive 5-FU, treatment with CT1501R prevented both the rise in ANC and rise in CFU-GM/femur associated with the vehicle control. All CT1501R treated animals maintained ANCs within one standard deviation of non-injected controls. It appears that CT1501R prevented the stress-induced and probably cytokine-mediated response to twice daily i.p. injections.

Overall, these data support a method of using CT1501R and the inventive compounds to accelerate the reconstitution of hematopoiesis following cytotoxic drugs or cytoreductive therapies.

We claim:

1. A method for treating a disease mediated by abnormal IL-1 signaling activity, comprising administering an effective amount of a compound wherein the compound has a formula:

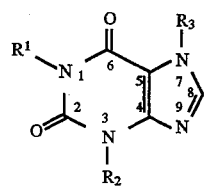

wherein:

$R_1$ is a substantially pure resolved R enantiomer ω-1, secondary alcohol-substituted alkyl ($C_{5-8}$) group; and $R_2$ and $R_3$ are independently hydrogen atom or an alkyl ($C_{1-12}$) or alkoxyl ($C_{1-12}$), or a pharmaceutical composition thereof.

2. The method of claim 1 wherein the compound is 1-(R)-(5-hydroxyhexyl)-3,7dimethylxanthine.

3. The method of claim 1 wherein the disease mediated by abnormal IL-1 signaling activity is selected from the group consisting of psoriasis, asthma, osteoporosis, alcoholic hepatitis, and premature labor secondary to uterine infection.

4. A method for treating psoriasis, asthma, osteoporosis, alcoholic hepatitis, or premature labor secondary to uterine infection, comprising administering an effective amount of a compound to an individual in need of such treatment, wherein the compound has a formula:

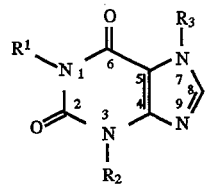

wherein:

$R_1$ is a substantially pure resolved R enantiomer ω-1, secondary alcohol-substituted alkyl ($C_{5-8}$) group; and $R_2$ and $R_3$ are independently hydrogen atom or an alkyl ($C_{1-12}$) or alkoxyl ($C_{1-12}$).

5. The method of claim 4 wherein the compound is 1-(R)-(5-hydroxyhexyl)-3,7-dimethylxanthine.

* * * * *